US008940477B2

(12) United States Patent
Johnson et al.

(10) Patent No.: US 8,940,477 B2
(45) Date of Patent: Jan. 27, 2015

(54) METHOD OF DETECTING BOTULINUM NEUROTOXIN AND ANTIBODIES THAT NEUTRALIZE BOTULINUM NEUROTOXIN ACTION

(75) Inventors: Eric A. Johnson, Madison, WI (US); Sabine Pellett, Madison, WI (US); William H. Tepp, Madison, WI (US); Gary E. Borodic, Cambridge, MA (US); David J. Beebe, Monona, WI (US); Amy Paguirigan, Seattle, WA (US)

(73) Assignees: Wisconsin Alumni Research Foundation, Madison, WI (US); Gary E. Borodic, Cambridge, MA (US)

( * ) Notice: Subject to any disclaimer, the term of this patent is extended or adjusted under 35 U.S.C. 154(b) by 1360 days.

(21) Appl. No.: 12/291,411

(22) Filed: Nov. 10, 2008

(65) Prior Publication Data

US 2012/0164657 A1     Jun. 28, 2012

Related U.S. Application Data

(60) Provisional application No. 60/968,522, filed on Nov. 8, 2007.

(51) Int. Cl.
*C12Q 1/00*     (2006.01)
*C12Q 1/68*     (2006.01)
*G01N 33/567*   (2006.01)
*C12Q 1/37*     (2006.01)

(52) U.S. Cl.
CPC .............. *C12Q 1/37* (2013.01); *G01N 2333/33* (2013.01)
USPC ................................ 435/4; 435/6.15; 435/7.2

(58) Field of Classification Search
None
See application file for complete search history.

(56) References Cited

U.S. PATENT DOCUMENTS

2004/0219619 A1 *  11/2004  Fernandez-Salas et al. .  435/7.32

OTHER PUBLICATIONS

Pellett et al FEBS Letters 581 (Sep. 2007) 480-4808.*
Dong, M., et al., (2004) Using fluorescent sensors to detect botulinum neurotoxin activity in vitro and in living cells. PNAS 101:14701-14706.
Lindstrom, M. and Korkeala, H. (2006) Laboratory diagnostics of botulism. Clin. Microbiol. Rev. 19:298-314.
Sapsford, K.E., et al., (2005) Biosensor detection of botulinum toxoid A and staphylococcal enterotoxin B in food. Appl. Environ. Microbiol. 71:5590-5592.
Schantz, E.J. and Kautter, D.A. (1978) Standardized assay for *Clostridium botulinum* toxins. J. Assoc. Off. Anal. Chem. 61:96-99.
Schiavo, G., et al., (1993) Botulinum neurotoxin F is a zinc endopeptidase specific for VAMP/synaptobrevin. J. Biol. Chem. 268:11516-11519.
Sharma, S.K., et al., (2005) Evaluation of lateral-flow *Clostridium botulinum* neurotoxin detection kits for food analysis. Appl. Environ. Microbiol. 71:3935-3941.
Sharma, S.K., et al., (2006) Detection of type A, B, E, and F *Clostridium botulinum* neurotoxins in foods by using an amplified enzyme-linked immunosorbent assay with digoxigenin-labeled antibodies. Appl. Environ. Microbiol. 72:1231-1238.
Stahl, A.M., et al., (2007) Primary cultures of embryonic chicken neurons for sensitive cell-based assay of botulinum neurotoxin: Implications for therapeutic discovery. J. Biomol. Screen. 12:370-377; Epub Mar. 1, 2007.
Yowler, B.C., et al., (2002) Botulinum neurotoxin A activity is dependent upon the presence of specific gangliosides in neuroblastoma cells expressing synaptotagmin I. J. Biol. Chem. 277:32815-32819.
Hall, Y.H., et al., (2004) Novel application of an in vitro technique to the detection and quantification of botulinum neurotoxin antibodies. J. Immunol. Meth. 288:55-60.
Keller, J.E., et al., (1999) Persistence of botulinum neurotoxin action in cultured spinal cord cells. FEBS Lett. 456:137-142.
Keller, J.E. and Neale, E.A. (2001) The role of the synaptic protein SNAP-25 in the potency of botulinum neurotoxin type A. J. Biol. Chem. 276:13476-13482.
Keller, J.E., et al., (2004) Uptake of botulinum neurotoxin into cultured neurons. Biochemistry 43:526-532.
Neale, E.A., et al., (1999) Botulinum neurotoxin A blocks synaptic vesicle exocytosis but not endocytosis at the nerve terminal. J. Cell. Biol. 147:1249-1260.
Lalli, G., et al., (1999) Functional characterization of tetanus and botulinum neurotoxins binding domains. J. Cell. Sci. 112:2715-2724.
Welch, M.J., et al., (2000) Sensitivity of embryonic rat dorsal root ganglia neurons to *Clostridium botulinum* neurotoxins. Toxicon 38:245-258.
Benatar, M.G., et al., (1997) Lack of effect of Miller Fischer sera/plasmas on transmitter release from PC12 cells. J. Neuroimmunol. 80:1-5.
Pellett, S., et al. (2007) A neuronal cell-based botulinum neurotoxin assay for highly sensitive and specific detection of neutralizing serum antibodies. FEBS, 581:4803-4808.
Zhou, W., et al., (2007) Cyclosporin A increases expression of matrix metalloproteinase 9 and 2 and invasiveness in vitro of the first-trimester human trophoblast cells via the mitogen-activated protein kinase pathway. Hum. Reprod. 22:2743-2750.

(Continued)

*Primary Examiner* — Albert Navarro

(57) ABSTRACT

A highly sensitive method of analyzing a sample for the presence or activity of botulinum neurotoxin (BoNT) or antibodies specific for botulinum neurotoxin is disclosed. In one embodiment, the method comprises the steps of preparing primary non-human mammalian or avian spinal cord cells, and exposing the cells to a test sample, in parallel with a control sample, and examining the extent of cleavage of the intracellular neuronal target protein in both the test and control sample.

16 Claims, 20 Drawing Sheets
(18 of 20 Drawing Sheet(s) Filed in Color)

(56) References Cited

OTHER PUBLICATIONS

Du, Y., et al., (2007) In-Cell Western analysis of Helicobacter pylori-induced phosphorylation of extracellular-signal related kinase via the transactivation of the epidermal growth factor receptor. Microbes Infect. 9:838-846.

Honma, M., et al., (2006) Identification of Novel Keratinocyte Differentiation Modulating Compounds by High-Throughput Screening. J. Biomol. Screen 11:977-984.

Duggan, M.J., et al. (2002) Inhibition of Release of Neurotransmitters from Rat Dorsal Root Ganglia by a Novel Conjugate of a *Clostridium botulinum* Toxin A Endopeptidase Fragment and Erythrina cristagalli Lectin. J. Biol. Chem.

\* cited by examiner

| ul PurTox | full length | stdev | cleaved | stdev |
|---|---|---|---|---|
| 10 | 75.2 | 2.1 | 24.8 | 2.1 |
| 20 | 69.9 | 4.2 | 30.1 | 4.2 |
| 30 | 61.3 | 3 | 38.7 | 3 |
| 40 | 55.9 | 1.8 | 43.5 | 1.8 |
| 50 | 55.2 | 3.1 | 44.8 | 3.1 |
| 60 | 54 | 2.7 | 46 | 2.7 |
| 70 | 47.7 | 2.5 | 52.3 | 2.5 |
| 80 | 47 | 1.9 | 52.9 | 1.9 | a b c

METHOD OF DETECTING BOTULINUM NEUROTOXIN AND ANTIBODIES THAT NEUTRALIZE BOTULINUM NEUROTOXIN ACTION

STATEMENT OF FEDERALLY SPONSORED RESEARCH

This invention was made with United States government support awarded by the following agency: NIH AI040026, CA104162US. The United States government has certain rights in this invention.

CROSS-REFERENCE TO RELATED APPLICATION

This application claims priority from U.S. provisional patent application Ser. No. 60/968,522 filed Nov. 8, 2007, incorporated by reference herein.

BACKGROUND OF THE INVENTION

Botulinum neurotoxin (BoNT) produced by neurotoxigenic clostridia are the most potent naturally occurring toxins known [Johnson, E. A. (2005) Topley and Wilson's Microbiology and Microbial Infections, eighth edition. 1035-1088]. Based on their antigenic specificity, BoNTs are distinguished into seven serotypes (A-G) [Gimenez, D. F., and Gimenez, J. A. (1995) Int. J. Food Microbiol. 27, 1-9], with BoNT/A, B and E accounting for nearly all recorded cases of human botulism [Johnson, E. A. (2005) Topley and Wilson's Microbiology and Microbial Infections, eighth edition, 1035-1088; Montecucco, C. and Molgo, J. (2005) Curr Opin Pharmacol. 5, 274-279]. BoNTs are zinc-containing metalloproteases of ca. 150 kDa consisting of a heavy chain (~100 kDa), and a light chain (~50 kDa) linked by a disulfide bond.

The C-terminal domain of the heavy chain functions in receptor binding on the neuronal cell surface, inducing endocytotic internalization of the toxin. Once inside the endosome, protonation causes membrane insertion and chaperone/channel formation of the heavy chain coupled to light chain unfolding and entry into the channel. This is followed by light chain conduction through the heavy chain channel and subsequent release of the light chain by disulfide bond reduction and light chain refolding in the cytoplasm of the cell [4, 5]. Light chains of BoNTs are zinc endopeptidases that target core proteins including SNAP-25, VAMP/synaptobrevin, and syntaxin 1 involved in trafficking and release of neurotransmitters [Blasi, J., et al. (1993) Nature, 365:160-163; Binz, T., et al. (1994) J Biol. Chem. 269:1617-1620; Schiavo, G., et al. (1995) J. Biol. Chem. 268:11516-11519; Schiavo, G., et al., (1995) J. Biol. Chem. 270:10566-10570; Montecucco, C. and Schiavo, G. (1994) Mol. Microbiol. 13:1-8; Yamasaki, S., et al. (1994) J Biol. Chem. 269, 12764-12772].

The high potency of BoNT, its high specificity for motor neurons, and the longevity of its action (up to several months) have facilitated the use of BoNT/A and /B as extremely valuable drugs for treatment of a myriad of neurological diseases, as well as for cosmetic treatments, with BoNT/A being the most prominent serotype currently used [Foster, K. A., et al. (2006) Neurotox. Res. 9:133-140]. Despite the effective use of BoNTs in clinical applications, the major adverse effect has been the formation of antibodies which render patients refractory to treatment and tachyphylaxis [Borodic, G. (2007) Facial Plast. Surg. Clin. North Am. 15:11-16; Dressler, D. (2004) Mov Disord: 19(Suppl 8) S92-S100; and Borodic, G., et al. (1996) Neurology. 46:26-29]. For example, 5 to 10% of patients with cervical, segmental or multifocal dystonia receiving repeated BoNT/A treatments were estimated to develop resistance to treatments due to the presence of circulating neutralizing serum antibodies [Dressler, D. (2004) Mov Disord. 19(Suppl 8) S92-S100; Borodic, G., et al. (1996) Neurology. 46:26-29]. Resistance to BoNT treatment can be confirmed in a clinical setting by test injecting BoNT into the patient's frontalis muscle, extensor digitorum brevis (EDB) or sternomastoid muscle [Borodic, G. E. (1999) Current Opinions in Otolaryngology and Head and neck Surgery. 7:219-225; Borodic, G. E., et al. (1995) Neurology 45:204; Kessler, K. R. and Benecke, R. (1997) Mov Disord. 12:95-99; Cordivari, C., et al. (2006) Mov Disord., 21:1737-1741; Dressler, D. and Rothwell, J. C. (2000) Eur Neurol. 43:13-16], and measuring compound muscle action potentials. However, patients are not routinely monitored for antibody formation during their treatment regime, because a sensitive assay that measures neutralizing antibodies in human sera is not commercially available [Sesardic, D., et al. (2004) Mov Disord. 19 (Suppl 8): S85-91]. Such monitoring is highly desirable in clinical trials of BoNTs as well as for currently approved therapies.

Several laboratory assays for the detection of BoNTs and BoNT specific antibodies have been developed. The in vivo mouse bioassay currently is the standard method to detect BoNT activity, and the only assay approved by the FDA [Hatheway, C. L. (1988) Laboratory Diagnosis of Infectious Diseases. Principles and Practice. (Balows A., Hausler Jr. W. J., Ohashi M., Turano, A., Eds.) pp. 111-133. Springer-Verlag, New York; Schantz, E. J. and Kautter, D. A. (1978) J. Assoc. Off. Anal. Chem. 61:96-99]. In this assay, mice are injected intraperitoneally or intravenously with toxin or toxin/antibody mixtures and observed for signs of toxicity and death. While this assay is well-established and quantitative, it is relatively insensitive and has well-known drawbacks including the need for a large number of animals and associated required facilities and expenses, the requirement for 2-4 days for results, nonspecific deaths, and the need to expose mice to a high degree of pain and distress.

Alternative in vitro assays include the mouse diaphragm assay or MDA [Hatheway, C. L. (1988) Laboratory Diagnosis of Infectious Diseases. Principles and Practice. (Balows A., Hausler Jr. W. J., Ohashi M., Turano, A., Eds.) pp. 111-133. Springer-Verlag, New York], enzyme-linked immunosorbent assays (ELISAs) and variations, immunoprecipitation assay (IPA), chemiluminescent slot blot immunoassay, electro chemiluminscence, radioimmunoassay, lateral flow immunoassays, endopeptidase assays and others [Lindström, M. and Korkeala, H. (2006) Clinical Microbiology Reviews 19:298-314]. All of these assays can be used to quantitate BoNT's in vitro and in foods and clinical samples [Hatheway, C. L. (1988) Laboratory Diagnosis of Infectious Diseases. Principles and Practice. (Balows A., Hausler Jr. W. J., Ohashi M., Turano, A., Eds.) pp. 111-133. Springer-Verlag, New York; Sharma, S. K., et al. (2006) Appl Environ. Microbiol. 72:1231-1238; Sharma, S. K., et al. (2005) Appl. Environ. Microbiol. 71:3935-3941; and Sapsford, K. E., et al. (2005) Appl Environ Microbiol. 71:5590-5592]. However, many have the drawback of high background, and most measure only one biological property of BoNT activity (binding of the toxin to antibody, or proteolytic activity in the endopeptidase assays). In order to reliably measure BoNT holotoxin activity and detect neutralizing serum antibodies, an assay should simulate all aspects of intoxication (i.e.: binding of the heavy chain binding domain to the cell surface receptor, endocytosis, channel formation, conductance of the light chain into the cell's cytosol and disulfide bond cleavage, refolding of the light chain, and proteolytic cleavage of the target protein within the cell by the light chain).

A more complete approach for the screening of neutralizing antibodies as well as potency determination of the holotoxin is the use of cell-based BoNT assays. Several cell-based assays have been developed, including continuous cell lines such as neuro-2a, PC12, or SK-N-SH cells [Schiavo, G., et al. (1993) J. Biol. Chem. 268, 11516-11519; Dong, M., et al. (2004) PNAS 101:14701-14706; Yowler, B. C., et al. (2002) J. Biol. Chem. 277:32815-32819; Benatar, M. G., et al. (1997) J. Neuroimmunol. 80:1-5], as well as primary neurons derived from chicken, mouse or rat spinal cord cells [Stahl, A. M., et al. (2007) J. Biomol. Screen. 12:370-377; Hall, Y. H., et al. (2004) J. Immunol. Methods. 288:55-60; Keller, J. E., and Neale, E. A. (2001) J. Biol. Chem. 276:13476-13482; Keller, J. E., et al. (1999) FEBS Lett. 456:137-142; Keller, J. E., et al. (2004) Biochem. 43:526-532; Neale, E. A., et al. (1999) J. Cell. Biol. 147:1249-1260; Lalli, G., et al. (1999) J. Cell. Sci. 112:2715-2724; Welch, M. J., et al. (2000) Toxicon 38:245-258]. Successful detection of BoNT can be achieved by by Western blot assay of the cleaved target protein [Yowler, B. C., et al. (2002) J. Biol. Chem. 277:32815-32819; Keller, J. E., and Neale, E. A. (2001) J. Biol. Chem. 276:13476-13482; Keller, J. E., et al. (1999) FEBS Lett. 456:137-142; Keller, J. E., et al. (2004) Biochem. 43:526-532; Lalli, G., et al. (1999) J. Cell. Sci. 112:2715-2724], by specific FRET sensors [Dong, M., et al. (2004) PNAS 101:14701-14706], or by neuronal activity testing [Benatar, M. G., et al. (1997) J. Neuroimmunol. 80:1-5; Hall, Y. H., et al. (2004) J. Immunol. Methods. 288:55-60; Neale, E. A., et al. (1999) J. Cell. Biol. 147:1249-1260; Welch, M. J., et al. (2000) Toxicon 38:245-258]. However, continuous cell lines exhibit very low BoNT sensitivities and therefore cannot be used for detection of serum antibodies.

Most prior art primary neuronal cell assays using pure BoNT/A preparations have been reported to exhibit sensitivities of up to 50 μM of BoNT/A (~250 to 750 mouse $LD_{50}$ units), which is not sufficient for detection of most human serum antibodies. One primary cell assay has been adapted to detect as little as 3 μM BoNT/A and protection by up to 0.001 IU/ml of Equine International sera by measuring [$^3$H] glycine release from primary rat spinal cord cells [Hall, Y. H., et al. (2004) J. Immunol. Methods. 288:55-60]. However, enhanced practicality and even higher sensitivity and specificity are desired for clinical and research applications.

DESCRIPTION OF THE DRAWINGS

The patent or application file contains at least one drawing executed in color. Copies of this patent or patent application publication with color drawings will be provided by the Office upon request and payment of the necessary fee.

FIG. 1 depicts a Western blot demonstrating inhibition of SNAP-25 cleavage in primary rat spinal cord cells by serum containing neutralizing antibodies. The –C contains no BoNT/A, the +C contains only BoNT/A and no serum, and samples 1-5 contain serial dilutions of serum and the same amount of BoNT/A as the +C.

FIG. 2 is a bar graph summarizing triplicates of the experiment presented in FIG. 1. The bars indicate inhibition of cleavage by serum containing neutralizing antibodies.

FIG. 3 is a Western blot illustrating the inhibition of SNAP25 cleavage by Toosendanin.

FIG. 4 is a set of four Western blots illustrating SNAP25 cleavage in primary rat spinal cord cells varying induction of the cells with KCl and concentration. The "previous protocol" is a previously published method that we replicated in our lab.

FIG. 5 is a table indicating increased SNAP25 cleavage correlating with increased amounts of PurTox™.

FIG. 6 describes percentage SNAP25 cleavage as a function of amount of PurTox™, purified BoNT/A.

FIG. 7 is a graph of percentage cleavage of the BoNT/A control as a function of amount of concentration of BoNT/A and is the control for the experiment presented in FIGS. 5 and 6.

FIG. 8 depicts differentiation of primary rat spinal cord cells over time. Cells were plated onto collagen coated cover slips and observed by light microscopy for up to 25 days after plating.

FIG. 9 depicts Western blots showing BoNT sensitivity of RSC cells. RSC cells were exposed to serial dilutions of BoNT/A (a), E (b), and B (c), and cell lysates were examined by Western blot for SNAP25 (for A and E) or VAMP (for B) cleavage.

FIG. 10 depicts protection against SNAP25 cleavage in RSC cells by human sera. RSC cells were exposed to A: a mixture of 125 pg BoNT/A and 25% human serum of 15 different patients, and B: a mixture of 12.5 pg BoNT/A and 25% of human serum #3 and #8, and the cell lysates were assayed for SNAP25 cleavage by Western blot. The +C represents toxin only controls and the –C represents cells not treated with toxin or serum.

FIG. 11 depicts sensitivity of RSC cells for antibody detection. RSC cells were exposed to a mixture of 125 pg BoNT/A and a (1) 1:200, (2) 1:400, (3) 1:800, (4) 1:1600, (5) 1:3200 dilution of human serum #4. A Western blot of SNAP25 cleavage (a) and a quantitative representation of densitometric analysis of three Western blots (b) are shown. The +C represents 125 pg BoNT/A without serum, and the –C contains no toxin and no serum.

FIG. 12 depicts spinal cord cells with dose response to BoNT/A. Due to significant autofluorescence or lack of a strong signal, it seems that these cells are not suitable for this technique, unless the protocol was optimized for these cells.

FIG. 13 depicts dose response of spinal cord cells with the new fixation protocol ICW on the top (a) and Western blot on the bottom (b). The p value for 0.125 pM in ICWs is 0.15, although there is a visible amount of cleaved SNAP25 on the Western, which is noticeably higher than either of the two lower concentrations.

FIG. 14 depicts neuro2a cells with or without toxin treatment for 48 hours. The fold induction between them is 1.65 and a p value of 0.008 between treated and untreated (control). A 1:25 dilution of the primary was done simultaneously and did not provide data that was significantly different between the two conditions.

FIG. 15 depicts neuro2a cells with primary and secondary antibody titrations, with treated cells only (a), and the fold increase of the treated cells over background (no primary) wells for each secondary dilution (b).

FIG. 16 depicts (a) normalized integrated intensity for each dose of toxin given with a 24 hour exposure and nuero2a cells. (b) The fold increase in signal as compared to the untreated cells for each dose of toxin). (c) Raw image of neuro2a cells. Bottom table, p values for each dose when compared with untreated cells, while Untreated cells were not significantly different from background (no primary).

FIG. 17 depicts Western blots stained with the cleaved SNAP-25 antibody in (a), and scanned on a laser scanner, while the same lysates were stained using total SNAP-25 and analyzed via chemiluminescence (b). The presumed bands of cleaved SNAP-25 were quantified for the blot using the cleaved SNAP25 antibody for (c), western blots and (d) ICW, both were normalized to the signal of the untreated cells:

FIG. 18 depicts fixation with a shorter PFA exposure time and less triton exposure time gave significantly improved results for ICWs. (a) A 1:50 dilution of primary gave a p value between 30 nM and untreated cells of 0.02, (b) a 1:75 dilution of primary gave a p value of 0.09, and (c) a 1:100 dilution of primary gave a p value of 0.99. The fold increase in signal between 30 nM treated cells and untreated cells in (a) is 2.6. This is a significant improvement over the previous protocol, in which a dose of 100 nM for 48 hours only gave a 2 fold induction in signal.

FIG. 19 depicts the blocking conditions. Tested were the Licor blocking buffer (with 0.1% Tween-20, Licor-T, or without, Licor), 10% goat serum in PBS with 0.1% Tween-20, or 3% BSA in PBS with 0.1% Tween-20. The Licor blocking buffer with Tween-20 have significantly lower background than any of the other conditions, and was what was used in all data presented here. The same titration of the primary antibody was performed as shown in FIG. 6, with goat serum with Tween-20 as the blocking buffer. No significant increase in signal above background was detected in any condition due to such high levels of nonspecific staining.

FIG. 20 depicts a set of bar graphs. Top row is 1 triton wash, (a) is 1:25 primary dilution, (b) is 1:50 primary dilution. Bottom row is 2 triton washes, (c) is 1:25 primary dilution, (b) is 1:50 primary dilution. The p values shown are the level of significance between either the 20 or 10 nM condition and untreated cells. The fixation and staining combination that gave the most sensitive readout of cleaved SNAP-25 is 1 triton wash, 1:25 dilution of the primary (a). This condition gave a 1.36 fold increase in signal for the 20 nM condition with respect to untreated cells, and a 1.21 fold increase for 10 nM.

Figure 23:
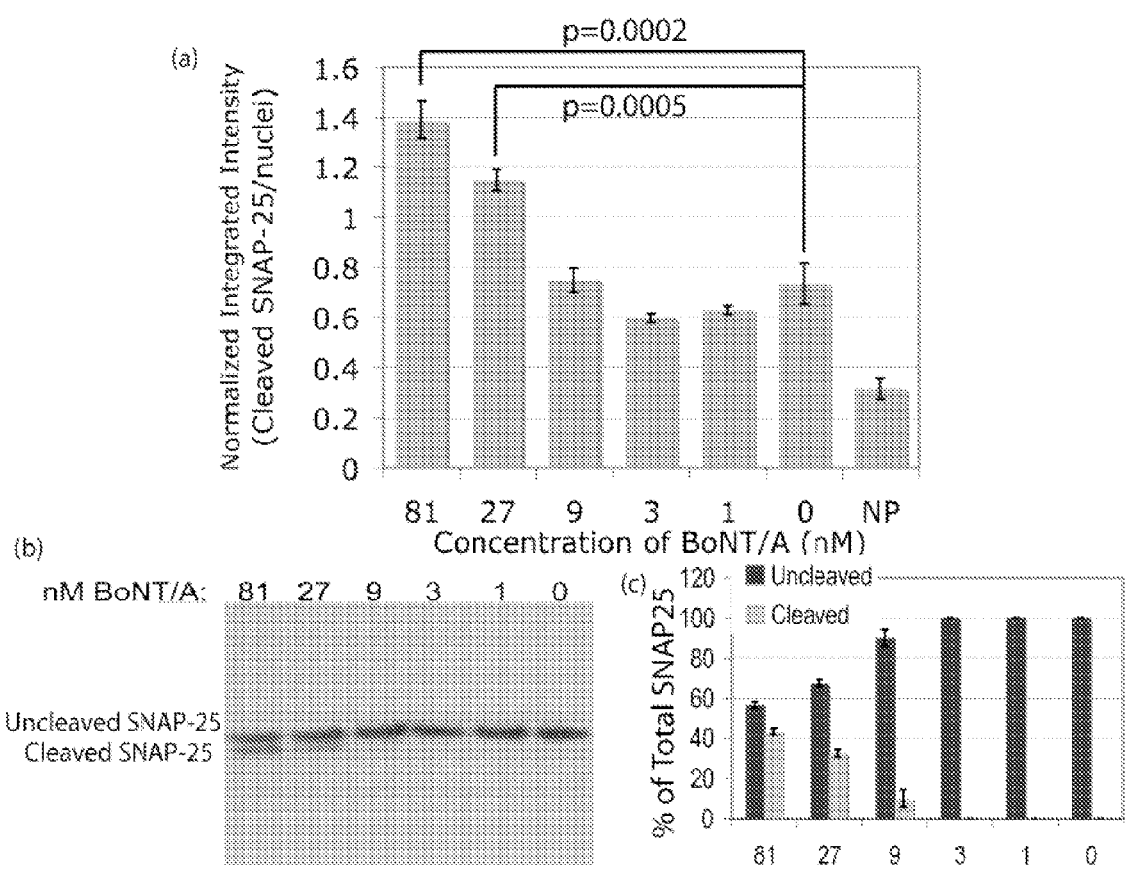

FIG. 23 depicts the dose response of neuro2a cells with the new fixation protocol ICW on the top (a) and Western blot on the bottom (b) with the quantification of the Western blot in (c). In this case, significance between the treated and untreated conditions was high for the 81 and 27 nM doses, which is consistent with the Western blot results as bands for cleaved SNAP25 in the lower concentrations are not visible. Very little cleaved was seen in the 9 nM condition and none in the 3 or 1 nM conditions, which is similar to the ICW results.

SUMMARY OF THE INVENTION

The present invention can detect as little as 33 fM BoNT (preferably BoNT A and E, ~0.1 mouse $LD_{50}$ units), and requires each step in the intoxication process as it measures changes in intracellular substrate cleavage. Therefore, all preceding steps of the intoxication process must have already occurred. In the Examples below using human serum samples, the usefulness of the assay in detection of neutralizing serum antibodies is presented and compared to the mouse lethality assay.

In one embodiment, the invention is a method of analyzing a sample for the presence or activity of botulinum neurotoxin (BoNT) or antibodies specific for botulinum neurotoxin, comprising the following steps: a) preparing primary non-human mammalian or avian spinal cord cells, and b) exposing the cells to a test sample, in parallel with a control sample, and examining the extent of cleavage of the intracellular neuronal target protein in both the test and control sample. Preferably the preparation of the primary spinal cord cells is in media that contains substantially no serum or growth inhibitors. In a preferred embodiment, the cells are rat cells and the sample is a biological sample selected from the group consisting of blood serum, blood plasma and whole blood.

In one preferred embodiment, the test sample is evaluated for the presence of neutralizing antibodies and the assay detects as little as 0.000091 IU of neutralizing antibody. In one preferred embodiment, wherein the test sample is evaluated for the presence or potency of botulinum neurotoxin and the assay detects as little as 33 fm of botulinum toxin.

In another embodiment, the present invention is a method of evaluating a sample for the presence and/or potency of a botulinum toxin inhibitor comprising the steps of: a) preparing primary mammalian or avian spinal cord cells, and b) exposing a first portion of the cells to a test sample and BoNT and examining the extent of cleavage of the intracellular neuronal target protein, wherein a reduction of the extent of cleavage compared to a second portion of the cells that have not been exposed to the test sample indicates that the test sample contains an inhibitor of botulinum toxin, preferably wherein the preparation of the primary spinal cord cells is in media that contains substantially no serum or growth inhibitors.

In one embodiment the test sample represents a first batch of toxin and is compared to a second test sample representing a second batch of toxin of known potency.

In a preferred embodiment, the present invention comprises the detection of cleavage is via ICW (In Cell Western). In another embodiment of the present invention is a kit for the detection and potency of botulinum neurotoxin, neutralizing antibodies specific to botulinum neurotoxin, or inhibitors of botulinum neurotoxin, wherein the kit comprises an aliquot of primary mammalian or avian spinal cord cells that have been calibrated so that the relationship between the amount of added botulinum neurotoxin and the amount of cleavage of an intracellular neuronal target protein has been calculated for the cells.

DESCRIPTION OF THE INVENTION

A. In General

*Clostridium botulinum* neurotoxins (BoNTs) A and B are widely used as a pharmaceutical to treat various neurologic disorders and in cosmetic applications. The major adverse effect of these treatments has been resistance to treatment after multiple injections. Currently patients receiving botulinum neurotoxin therapy and patients enrolled in clinical trials for new applications with new formulations of botulinum toxin need to be tested for the presence of neutralizing antibodies. Past methods have been thought to be relatively insensitive and sometimes nonspecific.

The tests described herein represents the closest approximation of the in vivo interactions that are essential to the pharmacologic action of botulinum toxin when used as a therapeutic agent. The neuronal cell assay of the present invention measures both external receptor binding, internalization, and lysis of cytoplasmic substrate (e.g. cleavage at SNAP-25 for BoNT A or VAMP/synaptobrevin for BoNT B).

This endpoint is thought to be the critical pharmacologic steps that are operative for most indications for which botulinum toxin is used in man.

The assay disclosed herein shows sensitivities to the detection of botulinum toxin that approach and surpass the best detection sensitivities of any animal based assay that has been presented to date. A high toxin sensitivity facilitates a more sensitive test for botulinum deactivation by neutralizing antibodies.

The present invention is a sensitive and specific method to detect botulinum neurotoxin (BoNT) and antibodies that neutralize BoNT action. In one embodiment, the present invention is a method of analyzing a sample for the presence or activity of botulinum neurotoxin (BoNT) or antibodies specific for botulinum neurotoxin comprising the following steps: a) preparing primary non-human mammalian or avian spinal cord cells and b) exposing the cells to a test sample, in parallel with a control sample, and examining the extent of cleavage of the intracellular neuronal target protein in both the test and control sample. The "control sample" for analysis of toxin activity would typically comprise an aliquot of the same primary non-human mammalian or avian spinal cord cells that have been exposed to controlled amounts of toxin using, preferably, the same amount of diluent. One would then be able to form a standard curve. For antibody detection, preferred controls would be control cells exposed to the same amount of toxin as the test cells wherein the control cells have no antibody. Preferably both kind of assays will include a sample with no toxin as a negative control.

The neuronal cell based assay disclosed herein simulates the pharmacologic effect occurring after in vivo injection of botulinum toxin preparations as they are thought to occur within peripheral nerve cells. Therefore, in another embodiment the invention is a method for research of characteristics of different botulinum neurotoxin preparations and subtypes, such as of determining ideal excipient concentrations to enhance penetration into nerve cells, evaluate new chimeric or hybrid types of Botulinum toxins, or recombinant forms of Botulinum toxin for clinical effects. The assay of the present invention can also be used to determine the pharmacokinetic rate of permeation of botulinum neurotoxin into nerve cells.

In one typical embodiment of the invention, the assay comprises the following steps:
a) Preparing primary spinal cord cells from non-human mammalian or avian fetal tissue, preferably E14 or E15 Sprague Dawley rat pups. One pregnant rat usually yields enough cells for 72 assays if used in the 24 well format, or over 300 assays if used in the 96-well format.
b) Exposing a sample of the neuronal cells to a test amount or a series of different test amounts of botulinum neurotoxin, preferably by addition of the toxin to the growth media, and incubation, preferably for 24 to 48 hours. Preferably, this exposure will allow one to develop a standard curve by calibrating the amount of toxin versus the extent of target cleavage.
c) Exposing, in parallel, a second sample of the neuronal cells to a test sample, wherein the test sample comprises botulinum neurotoxin, antibodies specific for botulinum neurotoxin, and/or inhibitors of botulinum neurotoxin.
d) Harvesting the cells, preferably by dissolving directly in SDS-PAGE gel loading buffer, and examining of the extent of cleavage of the intracellular neuronal target protein.

The extent of target protein cleavage increases with increasing amounts of toxin, until all target protein is cleaved. In the case of BoNT activity detection, a standard curve using known amounts of toxin will show the extent of cleavage with those known amounts of toxin. Therefore, the cleavage pattern of the unknown sample can be compared to that curve and the potency can be calculated by knowing the volume of unknown sample added.

In a typical assay, one might use 50% cleavage of the target protein as an endpoint, i.e.: 5.5 Units of BoNT/A result in 50% cleavage in a standard 48 h assay. Therefore if 10 ul of an unknown sample results in 50% cleavage, the sample has an activity of 5.5 Units/10 ul, or 550 Units per 1 ml. One typically uses different dilutions of the unknown sample, and obtain a linear does-response, in order to get valid results.

A preferred antibody titer is described in the Examples. Basically, the extend of target protein cleavage from an unknown sample is compared to the cleavage of the 'toxin only' control, and a decrease in cleavage signals the presence of neutralizing antibodies. If an antibody titer is desired, a known antibody-sample has to be run in parallel in the assay using serial dilutions of the antibody and a constant amount of toxin. The titer of the unknown sample can then be determined by correlation of the target protein cleavage pattern to the known sample.

B. Neuronal Cells of the Present Invention

The method requires mammalian or avian rodent neuronal cells in tissue culture as a target for the toxin, thereby requiring all steps of intoxication (receptor binding, internalization by endocytosis, cleavage of the disulfide bond between the heavy and light chain of the toxin, channel formation, guidance of the light chain of the toxin into the cytoplasm, refolding of the light chain, and cleavage of the target protein). The method assays for the action of botulinum neurotoxin by examining cleavage of the BoNT substrate target protein in the neuronal cells.

Regulatory agencies, including NIH, FDA, CDC, as well as currently used industry and academia have emphasized the need to find alternative methods to the mouse bioassay in order to reduce the use and suffering of animals and other drawbacks inherent to the mouse bioassay. Unlike other reported assays for detection of botulinum neurotoxin, the assay disclosed in this application represents a valid alternative to the mouse bioassay because it requires all steps of intoxication: has enhanced specificity and comparable sensitivity to the mouse bioassay, and is at least 10-fold more sensitive in detecting antibodies that neutralize BoNT activity, including in human sera. These properties have important utility in the performance of clinical trials for cosmetic and therapeutic uses of botulinum neurotoxins.

The assay of the present invention has been shown to yield excellent results using primary rat spinal cord cells. We envision that the rat spinal cord cells can be replaced by other types of non-human mammalian spinal cord cells, preferably rodent spinal cord cells, and most preferably mouse spinal cord cells. In another embodiment, one may wish to use avian, preferably chicken, spinal cord cells.

Pellett et al. FEBS, 2007, 581:4803-4808, incorporated by reference and repeated at Example V and Example I, disclose especially preferred methods for preparing rat spinal cord cells. Preferably, these spinal cord cells are prepared in media that contains substantially no serum or growth inhibitors compared to other cell-based assays resulting in no need for growth inhibitors and thereby providing optimal conditions for cell heath. The absence of serum prevents overgrowth of non-neuronal cells in the cell mixture. Example I discloses a culture method wherein the cells were cultured in culture medium [preferably Neurobasal medium supplemented with B27 and glutamax (Invitrogen)], at 37° C. in a humidified 5%-10% $CO_2$ atmosphere. The cells were allowed to differentiate in culture for at least 18 days, with bi-weekly changes of growth medium, before being used in the assay. Pellett et al., 2007, discloses a cell-isolation method based on Fitzgerald (1989), "Dissociated spinal cord—dorsal root ganglion cultures on plastic tissue culture dishes and glass coverslips and wells" in: *A Dissection and Tissue Culture Manual of the Nervous System* (Shahar, A., de Vellis, J., Veradakis, A. and Haber, B., Eds.), pp. 219-222, Alan R. Liss Inc., New York, incorporated by reference herein. Pellett et al., 2007, describes preferable modifications including culture medium modifications made to this prior art method.

Preferably, the cells are cultured in the following way:

General note: The method steps below describe a specific preferable example of isolation of spinal cord cells from rat. Applicants believe that one may substitute other non-human mammalian or avian species and obtain spinal cord cells that are suitable for the present invention. Similarly, many of the method steps below are substitutable with similar procedural steps that obtain the same result. For example, tools need not be autoclaved for exactly the amount of time shown and the animal model need not be anesthetized with $CO_2$. The most critical steps below involve the steps involving culture media. It is preferred that the culture media of the present invention is substantially serum free. It is preferable that the culture media is essentially free of serum or growth inhibitors such as 5'-fluoro-2'-deoxyuridine and uridine.

Autoclave all tools needed for 1 h+30 min drying time.

If using rat cells, order a timed pregnant Sprague Dawley rat to be at gestational age 15 (E15) the day of your prep (for example, we order E14 rats the previous day). Indicate arrival date on the order form. If using other non-human mammalian or avian species, one would acquire a set of fetal animals of the appropriate age. The age of the fetal animal is important, as cells from too young fetuses have not matured enough to do well in culture and too old fetuses have developed a hard spine making dissection very difficult. Appropriate age considerations are described in Fitzgerald (1989) and other literature for other species. One could use an E13 or E14 rat as well. We have used these rats before with no apparent change in the cells.

Anesthetize the rat with $CO_2$.

Completely wet the abdomen of the rat with 95% ethanol to avoid hair getting into the abdominal space when cutting.

Cut the abdominal skin back as much as possible with large scissors, starting as low as possible.

Rinse all hair off the scissors with 95% EtOH, then open the abdominal cavity with large scissors and large forceps, and extract the uterus containing the pups. Transfer the uterus to a sterile dish containing dissection media, and move into sterile hood.

In hood, dissect out the pups using small tweezers and decapitate using small scissors. Transfer the decapitated pups to a fresh dish containing dissection media.

Move the dish containing the pups under the scope at 0.75× magnification. Using two needle-point tweezers, carefully remove the skin off the back of the pups, then take out the spinal cords and transfer to a fresh dish containing dissection media.

Change the scope setting to 2.5× magnification, and carefully and completely remove all membranes and ganglia from the spinal cords. If the spinal cords were taken out intact, the membranes should come off in one or two large pieces.

Transfer the cleaned spinal cords to a fresh dish containing 4.5 ml dissection medium, and mince with small scissors or tweezers.

Transfer the minced spinal cords and all of the 4.5 ml solution into a sterile 15 ml conical tube and add 0.6 ml Trypsin LE.

Incubate at 37° C., 5% $CO_2$ for 20 min.

Remove all trypsin solution, and wash once with 15 ml dissection media.

Remove as much of the dissection media as possible, and add 1 ml of culture media. Triturate cells by pipetting up and down with a 1 ml pipette 10-12 times (try not create foam), just until most cells are dissociated.

Let any debris settle to the bottom of the tube (~3 min), and count cells by mixing 2 μl of cells with 38 μl of trypan blue (this will stain dead cells blue, while live cells will appear white), and count live cells.

Dilute cells to 400,000 cells per ml in culture medium, and plate 1 ml (400,000 cells) per well into collagen coated 24-well or 96-well dishes.

Incubate at 37° C., 5% $CO_2$ for 4-5 days, then replace media with fresh culture media.

After 2-3 weeks, the cells will be ready to be used in the BoNT-assay.

Materials:

Collagen coated 24-well or 96-well cell culture dishes (BD BioSciences)

Sterile solution basin, 55 ml: Fisher 730-004

TC-water: Gibco (Carlsbad, Calif.) 15230-162 (500 ml, 0.1 micron filtered, cell culture grade, endotoxin screened)

TrypLE: Gibco (Carlsbad, Calif.) 12605-010

Hepes: Gibco (Carlsbad, Calif.) 15630-080 (100 ml, 1 M)

Hanks balanced salt solution (HBSS): Gibco (Carlsbad, Calif.) 14170-112 (1×, 500 ml, 0.1 micron filtered, without calcium chloride, without magnesium chloride, without magnesium sulfate)

2.5 M Glucose: Sigma-Aldrich (St. Louis, Mo.) G8769 (45%, sterile, TC-tested)

B-27 supplement: Gibco (Carlsbad, Calif.) 17504-044 (50× stock, 10 ml)

Trypan blue: Sigma-Aldrich (St. Louis, Mo.) T-8154

Large scissors: Fine Science Tools (Foster City, Calif.) 14001-14

Large forceps: Fine Science Tools (Foster City, Calif.) 11001-12, 12 cm curved

Small scissors: Fine Science Tools (Foster City, Calif.) 14028-10, 10 cm surgical scissors, straight, sharp/blunt Small forceps: Fine Science Tools (Foster City, Calif.) 11050-10

Needle point tweezers: Fine Science Tools (Foster City, Calif.) 11252-20, 11 cm Dumont #5 Inox forceps NOTE: All the tools can be easily substituted as well.

Dissection media: HBSS, 10 mM hepes, 20 mM glucose (to 500 ml bottle of HBSS add 5 ml 1M Hepes and 4 ml 2.5 M glucose)

Culture media: Neurobasal (Invitrogen, Carlsbad, Calif.) supplemented with GlutaMAX™ (5 ml) and B27 (10 ml). Could substitute other serum-free neural basel media.

NOTE: Preferably, the method of the present invention does not use serum and growth inhibitors. The cells are treated to a gentle handling during dissociation. Additionally, in a preferred embodiment all membranes and ganglia are removed from the spinal cord prior to dissociation.

C. Methods of the Present Invention

The assay of the present invention is useful for examining a test sample for the presence of botulinum neurotoxin, antibodies specific to botulinum neurotoxin, and/or inhibitors of botulinum neurotoxin. A preferable biological test sample is a patient's serum, blood, plasma or tissue sample. However, other test samples are also envisioned, such as foods, potential inhibitors of BoNT, research and pharmaceutical preparations of botulinum toxins and chemical inhibitors and laboratory-produced antibodies (e.g., vaccines). The cultured neuronal cells of the present invention are examined to determine the relationship between added toxin, neutralizing antibody or inhibitor and amount of target cleavage (dose response). Preferably, the neuronal cells are prepared as described in the Examples.

One would examine a test sample for the presence of botulinum toxin by exposing the prepared cells described above to the test sample and examining cleavage of the intracellular neuronal target protein compared to cleavage produced by a toxin standard of known activity, preferably, as described in the Examples. We have successfully performed the assay with BoNT/A, BoNTA/B and BoNTA/E. However, the assay would work with all serotypes of BoNT. One would examine a biological or test sample for the presence of neutralizing antibodies specific for botulinum neurotoxin by determining whether the test factor sample contained factors that interfered with target cleavage. This is determined by comparing the target cleavage obtained from exposure of the neuronal cells to a combination of test sample and known amount of toxin with that of a control containing only the known amount of toxin.

Similarly, one would examine a test sample for inhibitors by determining whether a test sample contained factors that inhibited the target cleavage. Preferably, we envision that one would wish to examine proteins, peptides, and small molecules for their use as botulinum toxin inhibitors. Example II discloses the evaluation of toosendanin as an inhibitor.

The present assay is considerably more sensitive than other assays reported for primary cell lines and for continuous cell lines including neuroblastoma and PC12 cells. For example, in the present assay, one can detect as little as 1.5 pg in 0.3 ml (33 Fm level) of BoNT/A and BoNT/E toxin, which is approximately equivalent to 0.1 mouse LD50 unit.

We have shown that the system of the present invention can detect as little as 0.00009 IU of neutralizing antibodies, which is 10 times more sensitive than the currently-used mouse bioassay. A screen of the serum of 15 patients' sera using this assay revealed the presence of neutralizing antibodies in 5 patients, which correlates well with the clinical observation of lack of response to BoNT/A treatment in those patients. The serum of two more patients who had been refractory to BoNT/A treatments but did not receive any treatments in at least 10 years, yielded minimal protection in this assay using 125 pg of BoNT/A, but did clearly show protection when only 12.5 pg BoNT was used. These sera did not protect against BoNT/A toxicity in the mouse bioassay. All other serum samples represented controls from naïve patients who did not have antibodies and did not provide any protection using this assay.

In another embodiment, the present invention provides methods that take advantage of some of the special characteristics of the neuronal cell-based assay.

The assay described herein simulates the pharmacologic effect occurring after in vivo injection of botulinum toxin preparations as they are thought to occur within peripheral nerves. Therefore, the present invention can be used to determine ideal excipient concentrations to enhance penetration into nerve cells, evaluate new chimeric or hybrid types of Botulinum toxins, or recombinant forms of Botulinum toxin for clinical effects. Measurement of excipients is important in botulinum toxin, as human serum albumin has been thought to play a role in the pharmacologic effect of the material. The present invention can be used to determine ideal excipient concentrations, which can include excipient proteins, inclusive but not limited to hyaluronidase, albumin, recombinant serum albumin, as well as nonprotein based excipients such as zinc concentration, sodium concentration, PH, and other potential permeates.

This assay can also be used to determine the pharmacokinetic rate of permeation of botulinum toxin neurotoxin into nerve cells. This rate can be measured on a time dependent fashion, and a curve of penetration into the cell and cleavage of SNAP-25 can be used to create a pharmacokinetic model for cell penetration from different preparations of botulinum toxin. The model could be used to test enhancements involving genetic recombinant forms of botulinum toxin, or any structural modification to the protein which could enhance penetration and binding. The receptor can also be studied for sensitivity for various concentrations and molar concentrations of botulinum toxin which would be ideal for penetration and dilution. Formulation improvements may also include botulinum toxin cell binding enhancement, which can be directly measured by this assay. The assay can also be used to measure potential competitive binding agents to block penetration of botulinum toxin to the nerve cells in a time dependent fashion. Such agents could potentially be useful as protective pharmaceutical drugs for the treatment of botulinum toxication.

Preferred methods are described below:

In order to determine optimal excipient concentration on current and new pharmaceutical preparations of BoNTs, measured amounts of BoNT are mixed with different amounts of excipient and/or single excipient constituents in the same total volume. Spinal cord cells are exposed to these samples in parallel, and the extent of target protein cleavage is determined, preferably by Western blot. Differences in the cleavage pattern indicate that the excipient and/or a single or several constituents influence activity of the BoNT preparation tested.

In order to determine the kinetics of cell penetration and target protein cleavage, spinal cord cells are exposed to different concentrations of BoNT in the same volume, and to the same amount of BoNT in different volumes. The cell exposure time is varied for each concentration from 1 h to 24 h, and after exposure the cells are washed and incubated until 24 h. Cells are lysed, and target protein cleavage is observed by Western blot. The results of this indicate the kinetics of BoNT cell entry into nerve cells, and effects of BoNT concentration on cell entry. By labeling the toxin, the penetration into cells can also be observed live on a microscope.

The kinetics of intracellular cleavage may be examined by exposing the cells to different amounts of BoNT for a certain amount of time, followed by cell washes and incubation in culture medium for different time periods. Cells are lysed at the different times, and analyzed for target protein cleavage by Western blot. Increase in target protein cleavage indicates that BoNT is still actively cleaving the target protein present in the cells. These studies can be performed over the course of several months as well, to observe long-term effects of BoNTs.

The present invention is useful for examining formulation improvements, such as botulinum toxin cell binding enhancement, which can be directly measured by this assay. The assay can also be used to measure potential competitive binding agents to block penetration of botulinum toxin to the nerve cells in a time dependent fashion. Such agents could potentially be useful as protective pharmaceutical drugs for the treatment of botulinum toxication.

For example, the present invention would be useful for examining batches of botulinum toxins: Botulinum toxin batches, when manufactured, are determined using a standard mouse LD50 bioassay. This bioassay has been thought to have an error rate of 25% of measurement and on a vial-to-vial basis. It is envisioned that the present invention will be useful to test consistency of botulinum toxin batches for commercial production. These botulinum based pharmaceuticals could include any immunotype A through G, or any modifications thereof. The neuronal cell based assay does not involve the use of animals, therefore, has a humane advantage. Furthermore, the use of animal bioassays could be confirmed by release criteria using confirmatory bioassays such as the one described herein.

In another embodiment, the present invention is a kit for determination of potency of botulinum toxin (preferably in non-GMP and pharmaceutical preparations), neutralizing antibodies specific to botulinum toxin, and/or inhibitors of botulinum neurotoxin. In one embodiment, the kit comprises aliquots of the cultured rodent neuronal cells, preferably rodent cells, described above and directions for toxin, antibody and/or inhibitor detection. Full calibration of the cells is not necessary for every assay; however a positive control known toxin standards is needed. This control is preferably provided in the kit. Standards could also be provided for toxin potency determination.

A protocol with instructions will be a useful part of a kit. The protocol may vary depending on the users application, however, the kit will typically include an instruction sheet detailing the methods for cell handling, toxin and/or toxin inhibitor exposure, and sample processing. This will typically include the composition of media used on the cells, the precise parameters used for toxin exposure (buffer composition, total volume, incubation time), and cell harvesting procedure and information on analysis of the samples by Western blot (lysis buffer, best gels to use, antibodies for target protein detection, instructions for interpretation of data).

A typical sample protocol is as follows:

The cells may be shipped as a preserved, typically cryopreserved, sample and instructions should include cell dissociation. The cells are maintained in culture medium (Neurobasal supplemented with B27 and GUTAMAX, from Invitrogen) at 37 C, 5% CO2, with bi-weekly changes of medium. When removing or adding media, never directly pipette onto the cells, but carefully let the media run down the side of the well and aspirate media off the side of the well by tipping the plate. Preferably, one would only remove about 50% of the medium and replace with fresh medium.

In order to expose cells to BoNT, serial dilutions of the BoNT solution are prepared in a total volume of 0.3 ml in culture medium. Note that some constituents of the BoNT solution may affect the outcome of the assay, and therefore the solute to culture medium ratio should be kept constant. In addition, all solutions must be sterile, and certain solutes may be cytotoxic and may have to be tested for cytotoxic effects on the cells.

Pre-warm the prepared samples and standards to 37° C. The culture medium is carefully aspirated off the cells, and the pre-warmed samples and standards are added directly into the wells. The plates are returned to a 37° C., 5% $CO_2$ incubator for 48 h. After this incubation period, the medium is carefully removed and discarded.

The cells are lysed in 0.3 ml (for a 24-well plate) or 0.075 ml (for a 96-well plate) 1×LDS buffer (Invitrogen) or a similar SDS-PAGE sample buffer by directly adding the buffer onto the cells and scraping the cells off with the pipette tip. The samples are transferred to EPPENDORF tubes, heated to 95° C. for 10 min, and separated on a 12% NuPAGE Bis Tris gel in MES running buffer (Invitrogen) for analysis of BoNT/A or E, and on a 4-12% NuPAGE Bis Tris gel in MOPS running buffer (Invitrogen) for analysis of BoNT/B. (Other gels with similar resolution may be used to substitute.) It is a good idea to include a pre-stained protein marker on the gel and run the gel until the 25-30 kDa band has migrated to the bottom of the gel for BoNT/A, to ensure proper resolution of cleaved versus full length SNAP25.

The gels are transferred to a membrane by Western transfer. Cleavage of the BoNT target protein is detected by standard Western blot using anti SNAP25 or anti VAMP antibodies (recommended antibodies: from Synaptic Systems (Goettingen, Germany) and WESTERN BREEZE CHEMILUMINESCENT kit, Invitrogen, (Carlsbad, Calif.). The membranes are directly scanned on a chemiluminescent scanner or, if not available, exposed to film. The bands of cleaved versus full length protein are quantified using a quantification software, and the users samples are compared to the standard. The standards can be used to create a plot of cleaved/full length target protein versus Units of BoNT, and the Units per test sample can be read from this standard plot. This method can be easily adapted to other plate formats such as 96-well plates by increasing or reducing all volumes and cell numbers correspondingly.

D. Detection Methods Useful in the Present Invention

The present invention involves evaluation of the amount of cleavage of the botulinum neurotoxin target protein. The description above and Examples I-V disclose detection via standard Western blot analysis. This type of analysis has been very useful for us and is suitable for the present invention.

However, in one preferred embodiment, the present invention provides a detection system with significant advantages. Example VI shows the use of "in-cell Weserns" or "ICWs" for evaluation of target protein cleavage.

As Example VI discloses, the ICW system comprises the use of microfluidic methods for increased ease of high throughput analysis and sensitivity. The ICW technique uses quantitative immunocytochemistry and a laser scanner to provide an in situ measure of protein quantities in cells grown in microfluidic channels of arbitrary geometries.

Recently, techniques for performing ICWs using a laser scanner or plate reader have been applied to a variety of analyses [Zhou, W. H. et al. Hum Reprod (2007); Du, Y., Danjo, et al. Microbes Infect 9, 838-46 (2007); Honma, M. et al. J Biomol Screen 11, 977-84 (2006)]. In general, to perform an ICW, cells are grown in monolayer cultures using typical tissue culture protocols and then fixed and stained just as for immunocytochemistry using fluorescent secondary antibodies. Using commercially available laser scanners, the total fluorescent signal from a well of multiwell plate, preferably a 96 well plate, is determined and normalized to a loading control such as β-actin or DNA content. With the appropriate controls needed to correct for issues like background fluorescence, and careful image processing, a quantitative measurement of the changes in relative levels protein expression between conditions can be determined.

The ICW technique does not rely on obtaining and processing sufficient amounts of cell lysate or performing gel electrophoresis and blotting procedures like traditional gel-based Westerns. Though it does not typically provide resolution sufficient to detect localization of proteins of interest it is therefore not subject to the level of experimenter bias that occurs when using microscopy-based ICC methods.

EXAMPLES

Example I

Sensitivity of Rat Spinal Cord Cells Assay in Detecting Neutralizing Serum Antibodies Purpose:
To determine the sensitivity of the rat spinal cord cells assay in detecting neutralizing antibodies from human serum and comparing it to the mouse protection assay.

Materials and Methods:
Primary rat spinal cord cells were isolated from Sprague Dawley rat pups at a gestational age of E15 and were cultured in collagen coated 24-well dishes (BD BioSciences) using culture medium (Neurobasal medium supplemented with B27 and glutamax (Invitrogen)), at 37° C. in a humidified 5% $CO_2$ atmosphere. The cells were allowed to differentiate in culture for at least 18 days, with bi-weekly changes of growth medium before being used in the assay.

A human serum sample from a patient repeatedly treated with BoNT/A and somewhat refractory to treatments was used in this assay. Triplicate samples of mixtures of serum dilutions (as indicated in Table 1) and 125 pg BoNT/A in a total volume of 300 μl of culture medium were pre-incubated at 37° C., 5% $CO_2$ for 1 h, and rat spinal cord cells were exposed at 37° C. in a humidified 5% $CO_2$ atmosphere for a time period of 48 h. The cells were harvested by lysis in 1×LDS buffer (Invitrogen), and analyzed by SDS-PAGE gel electrophoreses on 12% NuPAGE Novex Bis-Tris gels in NuPAGE MOPS running buffer (Invitrogen), followed by Western blot onto an Immobilon PVDF membrane (Millipore). Full-length and cleaved SNAP25 were detected by probing the membrane with a monoclonal antibody to SNAP25 (Synaptic Systems), and using the chemiluminescent Western Breeze kit (Invitrogen).

The same dilutions/toxin mixtures were assayed in the standard mouse protection assay, using two mice per dilution. The mouse protection assay was also repeated independently using the following serum dilutions: 1:80, 1:120, 1:160, and 1:200 and 125 pg of BoNT/A (10 $LD_{50}$ units).

Results:
In the mouse protection assay, the mice receiving injections containing serum dilutions greater than 1:200 all died the same day of injection. The mice receiving injections containing serum diluted 1:160 survived for one day, but died within 24 h. Of the mice receiving injections containing serum diluted 1:120, 1 mouse died within 24 h and the other mouse survived. The mice receiving injections containing serum diluted 1:80 both survived. Based on these results, the serum was calculated to contain approximately 0.4 IU (International Units) per ml.

Figure 1:
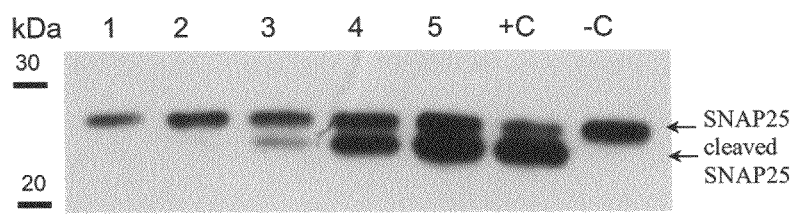
Figure 2:
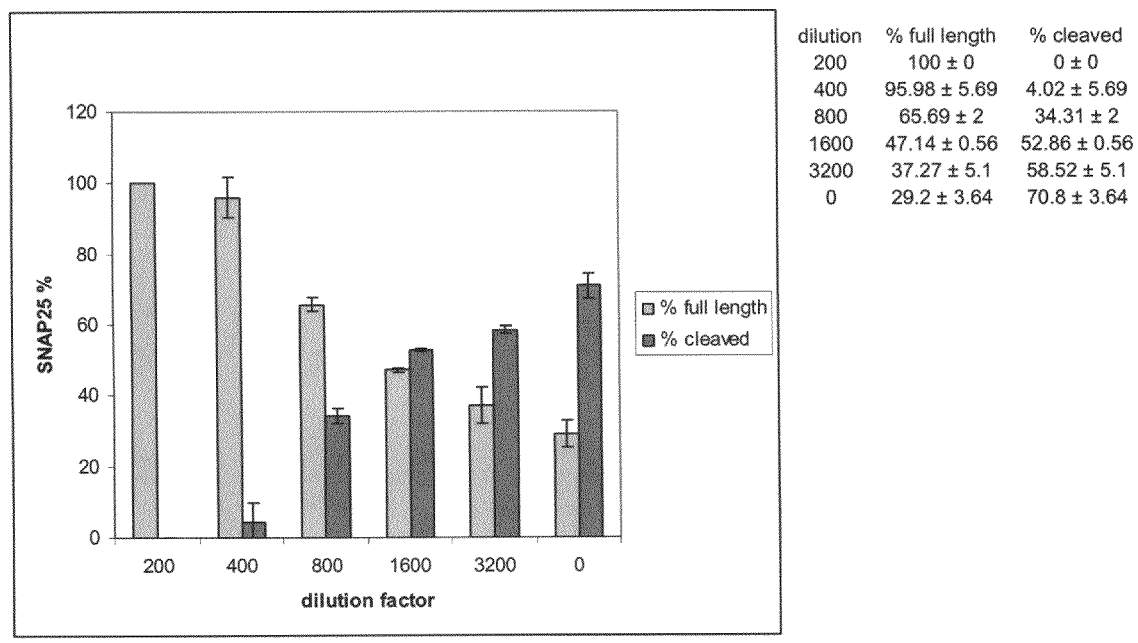

In the primary rat spinal cord assay, SNAP25 cleavage was fully protected when serum dilutions of 1:400 and 1:800 were used, and very obvious protection was observed with a dilution as low as 1:1600. A picture of a representative Western blot is shown in FIG. 1, and the triplicates of the experiment are summarized in FIG. 2. Based on above mouse protection assay, the 300 μl of a serum dilution of 1:3200 used in the assay contain approximately 0.00009 IU, which represents the detection limit of this assay as it is currently performed. These results were also confirmed by a blinded study using triplicates of serum dilutions up to 1:200, and all dilutions were correctly assigned to the respective samples seen in the Western blot (data not shown).

TABLE 1

| sample # | BoNT/A | Serum dilution |
|---|---|---|
| 1 | 125 pg | 1:200 |
| 2 | 125 pg | 1:400 |
| 3 | 125 pg | 1:800 |
| 4 | 125 pg | 1:1600 |
| 5 | 125 pg | 1:3200 |
| +C | 125 pg | 0 |
| −C | 0 pg | 0 |

Conclusions:
Since the rat spinal cord cell assay clearly detected protection against SNAP25 cleavage at a 1:1600 dilution, whereas the mouse protection assay required a 1:120 dilution, this assay is about 10 times more sensitive in detecting neutralizing serum antibodies than the mouse protection assay. In addition, these data indicate that this assay can be standardized and used to quantify the amount of neutralizing BoNT/A antibodies in human serum samples. Refining the assay will likely make it even more sensitive, as significant SNAP25 cleavage is consistently observed with as little as 15 pg BoNT/A (almost 10 times less than used in this assay), and using a smaller amount of toxin will increase the sensitivity of the protection assay.

Example II

Toosendanin as an Inhibitor

Introduction:
This experiment examined whether toosendanin protects against BoNT/A induced SNAP25 cleavage in the RSC (rat spinal cords cells assay) assay, as it does in mice.

Materials and Methods:
Rat spinal cord cells were prepared as described (Pellett et al., 2007) in 24-well dishes. One well of the cells was exposed to 500 pg BoNT/A combined with 500 μM Toosendanin (Toos), a second well was exposed to 500 pg BoNT/A (+C), and a third well contained culture medium only (−C). The cells were incubated for 24 h at 37° C., 5% $CO_2$. The cells were analyzed by Western blot as described (Pellett et al., 2007).

Figure 3:
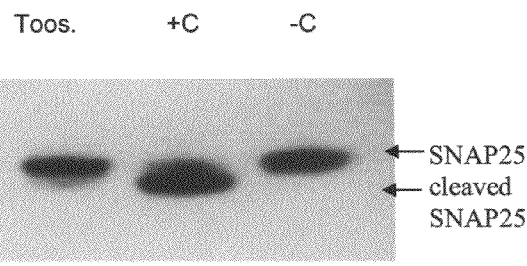

Results:
Referring to FIG. 3, in the Toosendanin sample, only full-length SNAP25 was detected, while in the positive control (BoNT/A only), almost all SNAP25 was appeared as the cleaved band. These results were reproducible (not shown).

Conclusion:
Toosendanin protects against BoNT/A induced SNAP25 cleavage in the RSC assay.

REFERENCES

Pellett S., Tepp W. H., Clancy C. M., Borodic G. E., and Johnson E. A. (2007). A neuronal cell-based botulinum neurotoxin assay for highly sensitive and specific detection of neutralizing serum antibodies. *FEBS letters*, in press. (Received 7 Aug. 2007; revised 29 Aug. 2007; accepted 31 Aug. 2007), also attached in $1^{st}$ section and as pdf.

Keller J. E., Cai F., and Neale E. A. (2004). Uptake of botulinum neurotoxin into cultured neurons. *Biochem.* 43: 526-532.

Example III

High Throughput Format

The purpose of this study was to determine whether a 96-well format of the rat spinal cord cells (RSC) assay will yield an equivalent sensitivity to BoNT/A as the 24-well format. A 96-well format would have the advantage of dramatically increasing the number of testing wells derived from one rat (from about 70 to about 300 or more), and of decreasing the amount of serum or testing compound required for an assay by about 6-fold (less than 0.3 ml will be adequate for titer determination). In addition, we hypothesized that decreasing the cell sampling size will increase sensitivity to BoNTs.

In addition, the current protocol for cell preparation (Pellett et al., 2007) was compared to the previously used protocol.

Materials and Methods:

Rat spinal cord cells were prepared, and toxin assay was performed essentially as described, except that the cells were seeded into collagen coated 96-well plates (BD Biosciences) at a density of 100,000 cells/well (Pellett et al., 2007). The cells were exposed to 125, 25, 5, 1, and 0.2 pg of BoNT/A (1 mouse LD50 Unit per 12.5-15 pg) in a total volume of 50 µl of culture medium, as described before. Exposure was for 48 h at 37° C., 5% $CO_2$. In parallel, the cells were also exposed to the same amounts of toxin in HBSS (Hanks balanced salt solution, Invitrogen) supplemented with 80 mM KCl for 10 min., followed by two washes of the cells in culture medium and incubation for an additional 48 h at 37° C., 5% $CO_2$. Each dilution was tested in duplicates. The cells were harvested in 75 µl of 1×LDS lysis buffer (Invitrogen), and 10 µl was analyzed by Western blot as described (Pellett et al., 2007).

In order to compare the current cell preparation protocol with the previously used protocol (Keller et al., 2004, supra and Hall et al., 2004, supra) cells were also plated into collagen coated 96-well plates (BD Biosciences) at the same density, but in DMEM supplemented with 5% inactivated horse serum and B27 (all from Invitrogen). After 5 days, medium was changed and 15 µg/ml 5'-fluoro-2'-deoxyuridine (FdU) and 35 µg/ml uridine (both from SIMA) were added to inhibit cell proliferation. Medium was changed every 5 days for three weeks, at which point the cells were used in the assay, using the same toxin dilutions as for the cells prepared by the current protocol. The cells were harvested in 75 µl of 1×LDS lysis buffer (Invitrogen), and 20 µl and 35 µl were analyzed by Western blot as described (Pellett et al., 2007).

Figure 4:
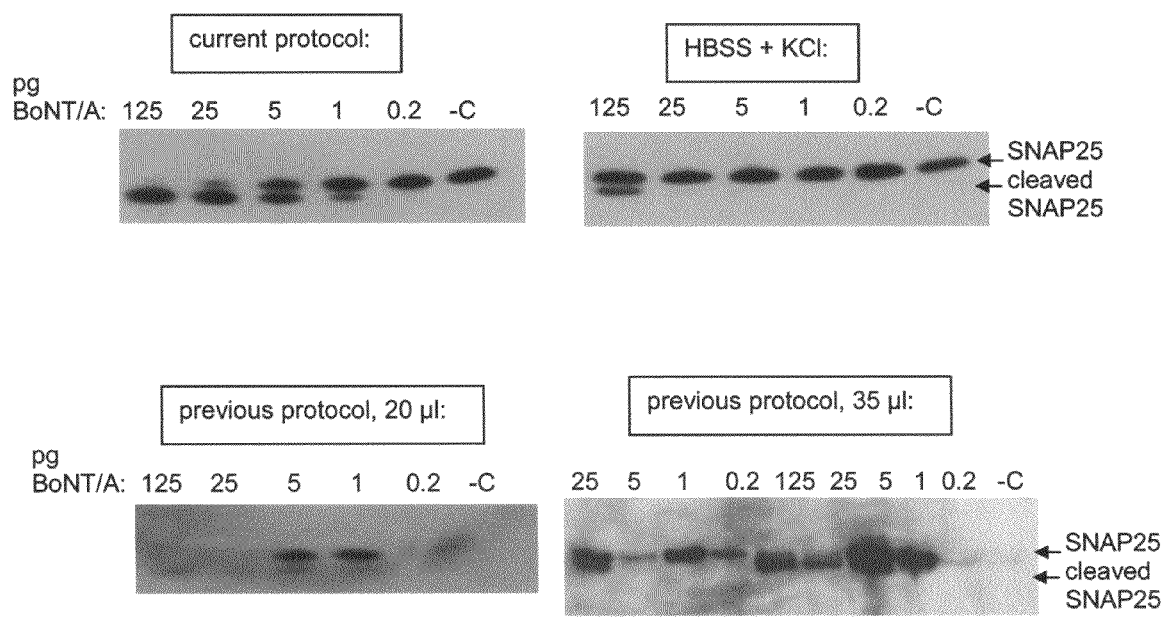

Results:

Referring to FIG. 4, only cleaved SNAP25 was detected when 125 pg BoNT/A were used, and about 70-80% of cleaved SNAP25 was observed with 25 pg BoNT/A. About 50% of full length and cleaved SNAP25 was observed with 5 pg BoNT/A, 70-80% of full length SNAP25 when 1 pg of BoNT/A was used. No cleaved SNAP25 was observed with 0.2 pg of BoNT/A.

Induction of the cells with KCl resulted in detection of about 30% cleavage with 125 pg BoNT/A, and no detection with lower concentrations. The duplicates of all samples resulted in the same cleavage pattern (not shown).

The signal on the Western blot of the cells prepared by the old method was too weak to determine the extend of SNAP25 cleavage when 20 µl of the samples were examined. Microscopic inspection of the cells prior to the assay showed that the cells were healthy. Examination of 35 µl of the cell lysates resulted in detectable signals in most samples, however, there was great variation in the signal intensities of the different samples. In addition, the signal was only detected after a 30 min exposure to film (maximum time), whereas the Westerns of samples prepared by the current protocol require only a 1 min film exposure and thus result in much cleaner figures. There also was considerable variation between duplicate sample containing the same amount of toxin: About 20-60% of cleaved SNAP25 was detected with 25 pg, 0-10% with 5 pg, and none with lower toxin amounts.

Conclusion:

The 96-well format resulted in an approximately 6-fold increase in sensitivity compared to the 24 well format (Pellett et al., 2007). This is corresponding to the 6-fold decrease in volume during the toxin assay. These data indicate that the 96 well format can be used instead of the 24-well format for toxin assays and antibody titer determination without a decrease in sensitivity. This will result in a significant decrease in the serum quantity requirement, as well as a significant increase in the number of cell samples per rat, making the 96-well format optimal for antibody detection. Some applications may require a larger testing volume, and for those the 24-well or even a 6-well format will be optimal.

The old cell preparation protocol resulted in a weak and inconsistent signal on the western blot. This is probably due to differences in the cells. While the cells appeared healthy, they appeared as a single monolayer of cells as compared to the more complex networking observed in the cells prepared by the current protocol. While SNAP25 cleavage could be detected when the maximum amount possible was examined on western blots, there was considerable variation in signal strength as well as in SNAP25 cleavage between samples. Therefore, using the old cell preparation protocol may not be applicable to a 96-well format, and may not be optimal in a 24-well format as well. In addition, it would require an additional step of determination of total protein concentration to achieve consistent signals on a Western blot. The sensitivity of cells prepared by the old protocol appears to be at least 10-fold lower than that of cells prepared by the current method.

Example IV

Purified BoNT (PurTox™) Blinded Trial

Purpose:

To examine the accuracy of the current primary rat spinal cord cells assay protocol in determining global change PurTox™ potency.

Materials and Methods:

The cell based assay was performed as described before (see earlier report). The following amounts of PurTox™ were tested: 10, 20, 30, 40, 50, 60, 70, and 80 µl (1, 2, 3, 4, 5, 6, 7, 8 Units) in a total volume of 300 µl of culture medium. The PurTox™ samples were tested in triplicates. In addition, 12.5, 31, 62.5, 94, and 125 pg (corresponding to 1, 2.5, 5, 7.5, and 10 mouse LD50 units) of BoNT/A lab stock were tested in parallel. Incubation of cells with toxin was for 48 h, and the cell lysates were prepared as described and analyzed by Western blot and quantification of the SNAP25 bands as described before (see earlier report). The potency of the BoNT/A lab stock was estimated by the mouse bioassay using a total of 10 mice at 5 different dilutions (5, 10, 15, and 20 pg of BoNT/A per mouse).

Figures 5, 6:
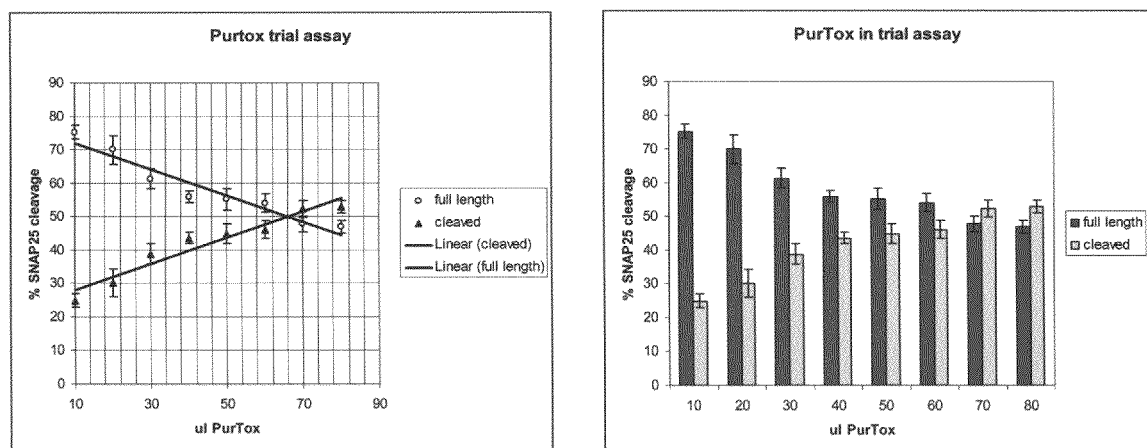
Figure 7:
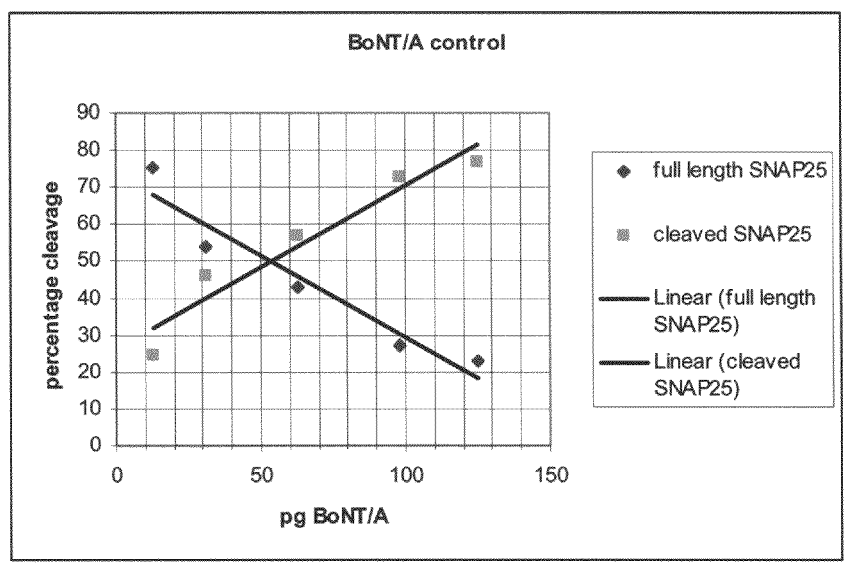

Results:

FIGS. 5, 6 and 7 summarize the results for the PurTox™ samples (FIGS. 5 and 6), and the BoNT/A control (FIG. 7). As can be seen in FIG. 5, there was a good correlation of increasing SNAP25 cleavage and increasing amounts of PurTox™. The relationship was linear throughout the range tested, and standard deviations were small.

Based on the mouse bioassay, the potency of the BoNT/A lab stock was estimated to be approximately 10 pg/$LD_{50}$. The PurTox™ resulted in 50% cleavage of SNASP25 at 65 µl, and the BoNT/A stock resulted in approximately 50% cleavage at 53 pg BoNT/A (about 5.3 $LD_{50}$ Units). Based on this, the PurTox™ titer was estimated at about 82 IU/vial.

Discussion:

These data represent the variation of PurTox™ activity determination within one assay. The assay was performed blindly, excluding the possibility of user error in band quantification. While the standard errors are relatively small indicating the ability to differentiate between 1 Unit of PurTox™, the relationship of SNAP25 cleavage with increasing amounts of toxin was only linear in the range of 1 to 4 Units. This may be in part due to technical challenges (one of the Western blots contained some uneven bands). However, it is apparent from these data that this assay in its current format can easily differentiate between samples differing in 2 to 3 Units across the range tested, taking into consideration variations in the quality of Western blots.

Since the current format of testing PurTox™ in this assay was to use only 1-8 Units per assay, the results have to be multiplied by 10 to determine the amount of PurTox™ per vial. This greatly increases the variation of the assay in its current format. However, this assay has the advantage over the mouse bioassay that the assay conditions can be adjusted to best fit the purpose. In this case, adjusting the conditions such that the PurTox™ can be tested across a range of 20-30 Units would be most beneficial and likely result in very low standard errors. The optimal assay conditions and range to be tested will have to be determined in future research. In addition, future research is required to test the variation across different assays using the same samples, and to determine the best control/standard to be used in this assay for calculation of the final titer.

The estimation of the titer is based on a lab-stock preparation of BoNT/A (not containing adjuvant), and the potency of that stock was estimated from a small number of mice and not determined in detail. Future research will determine the best standards to be used in this assay, and how many standards are required per assay for accurate titer determination.

Example V

A neuron cell-based botulinum neurotoxin assay for highly sensitive and specific detection of neutralizing serum antibodies (Pellett, et al., FEBS Letters 581 (2007) 4803-4808, incorporated by reference herein).

Materials and Methods:

Botulinum Neurotoxin and Mouse Bioassay:

Pure Botulinum neurotoxin (BoNT) A, B, and E (150 kDa) were prepared from *C. botulinum* strains Hall A hyper, Okra B, and Beluga E as previously described [40, 41]. The toxins were dissolved in phosphate buffered saline, pH 7.4 and 40% glycerol, and stored at −20° C. until use. Activity of the BoNT/A, /B, and /E preparations were determined by the mouse bioassay [Hatheway, C. L. (1988) Laboratory Diagnosis of Infectious Diseases. Principles and Practice. (Balows A., Hausler Jr. W. J., Ohashi M., Turano, A., Eds.) pp. 111-133. Springer-Verlag, New York; Schantz, E. J. and Kautter, D. A. (1978) J. Assoc. Off. Anal. Chem. 61:96-99], and specific toxicity was about $10^8$ mouse $LD_{50}$ Units/mg.

To estimate the titer of serum samples by mouse lethality assay [Hall, Y. H., et al. (2004) J. Immunol. Methods. 288: 55-60], 75 µl of serum were pre-incubated with 125 pg (and indicated dilutions) of BoNT/A in a total volume of 0.3 ml for 1 h. Each dilution was injected intraperitoneally into at least 2 mice, and the mice were observed until death for up to 4 days.

Human Sera Samples:

Human sera samples from patients repeatedly treated with BOTOX® who have demonstrated complete secondary resistance (non response), partial reduction in response, and continued effective responses were obtained from clinics after patient consent. An additional serum sample from a subject who received three doses of the pentavalent vaccine 16 years ago was analyzed (#11). All sera were stored at −20° C. until use and subsequently at 4° C. Table 2 summarizes the relevant medical histories of the patients. The sera were labeled 1-15, and were used in a blinded manner.

Primary Rat Spinal Cord (RSC) Cells:

The preparation of spinal cord cells was based on a previously described protocol with modifications as described [Fitzgerald, S. C. (1989). In: A Dissection and Tissue Culture Manual of the Nervous System. (Shahar, A., de Vellis, J., Vernadakis, A., Haber, B., Eds), pp. 219-222. New York: Alan R. Liss Inc.]. A pregnant Sprague Dawley rat (Harlan Sprague Dawley) at the gestational stage of E15 was euthanized by exposure to $CO_2$, and the uterus containing the pups was removed and placed into a dish containing dissection medium (Hanks balanced salt solution, 10 mM HEPES, 20 mM glucose (Invitrogen)). Working in dissection medium, the pups were removed from the uterus, immediately decapitated, the spinal cords were dissected out of the pups, and the membranes and ganglia surrounding the spinal cords were removed. The spinal cords were transferred to 4.4 ml of fresh dissection medium, minced, and transferred to a sterile 15 ml tube. 600 µl of TrypLE express (Invitrogen) was added, and trypsinization was allowed to take place for 20 min. at 37° C. in a 5% $CO_2$ atmosphere. The trypsin solution was removed and the spinal cords were washed once by addition of 15 ml of dissection medium. After the tissue settled to the bottom of the tube, the dissection medium was removed and 1 ml of culture medium pre-warmed to 37° C. (Neurobasal medium supplemented with B27, glutamax, and penicillin/streptomycin (all from Invitrogen)) was added. The cells were dissociated by pipetting up-and-down 10-12 times, and live cells were counted by trypan exclusion assay. 400,000 cells were plated into each well of collagen coated 24-well dishes (BD BioSciences). The cells were allowed to differentiate in culture at 37° C. in a humidified 5% $CO_2$ atmosphere for at least 18 days with bi-weekly changes of culture medium before they were used in the toxin assay. For microscopy, cells were plated onto collagen coated cover slips (BD BioSciences).

TABLE 2

Patient histories

| Patient | BoNT/A Exposure and Indication | Response History | Results of remote Point Testing* (20 Units) | Mouse bioassay |
|---|---|---|---|---|
| 1 | Over 12 injections for the Treatment of Glabellar Wrinkles (Botox) | Excellent result for 7 years followed by complete loss of effect | Frown lines not responsive | Negative |
| 2 | Control | Control | Control | Control |
| 3 | Essential blpeharsoapsm-injections between 1989-1992 (50-100 U Botox | Secondary none response in 1993. Botox nor Dysport | No effect on frontalis muscle (positive for resistance) | Positive |
| 4 | Cervical dystonia-16 injections between 1992-1996 (200-300 U Botox) | Substantial Secondary reduced response | No effect (positive for resistance) | Positive |
| 5 | Control | Control | Control | Control |
| 6 | Control | Control | Control | Control |
| 7 | Cervical dystonia 200-250 U of Botox over 3 month intervals 1995-1998 | Complete loss of response after 3-4 years to type A neurotoxin, now treated with type B | No effect (positive for resistance) | Positive |
| 8 | Cervical dystonia, receive 8 injections since 1991 | Loss of response after 4 years 9secondary non-responder) | ND | Positive |
| 9 | Cervical Dystonia, treated with 200-300 units over 14 years | Retains an excellent response | Sternomastoid shrinks with injections | Negative |
| 10 | Control | Control | Control | Control |
| 11 | Vaccinated Subject (three doses of pentavalent vaccine in 1991-1992) | no response in remote point test | No effect on frontalis muscle in 2004 | — |
| 12 | Control | Control | Control | Control |
| 13 | Cervical dystonia, 8 injections between 1991-1995 | Response 50% reduced since initiated (secondary reduced responder) | No effect or substantially reduced effect on frontalis muscle | ND |
| 14 | Control | Control | Control | Control |
| 15 | Essential blepharospasm, | continues to have benefit from repeated injections | Frontalis muscle weak after injection | Negative |

Cell-Based BoNT Assay:

After the differentiation period, various quantities of BoNT were added to culture medium in a total volume of 300 µl per well, followed by incubation at 37° C. in a humidified 5% $CO_2$ atmosphere for 48 h. To test for serum antibody neutralization, 75 µl of serum (or dilutions of serum in culture medium where indicated) were pre-incubated with 125 pg of BoNT/A (or as indicated) in a total volume of 300 µl per sample at 37° C., 5% $CO_2$ for 1 h prior to exposure of the cells. After 48 h, the cells were lysed in 150 µl of 1×LDS lysis buffer (Invitrogen). The samples were analyzed by SDS-PAGE gel electrophoresis on 12% NuPAGE Novex Bis-Tris gels in NuPAGE MOPS running buffer (Invitrogen), followed by transfer onto an Immobilon PVDF membrane (Millipore). Full-length and cleaved SNAP25 or VAMP were detected with a monoclonal antibody to SNAP25 or VAMP1 (Synaptic Systems) and the chemiluminescent Western Breeze kit (Invitrogen) and exposure to X-ray film (Kodak). To quantitate full length and cleaved SNAP25 bands, the films were scanned on a Gel DOC system (BioRAD), and the bands were quantified by densitometry using Quantity One software (BioRAD).

Figure 8:
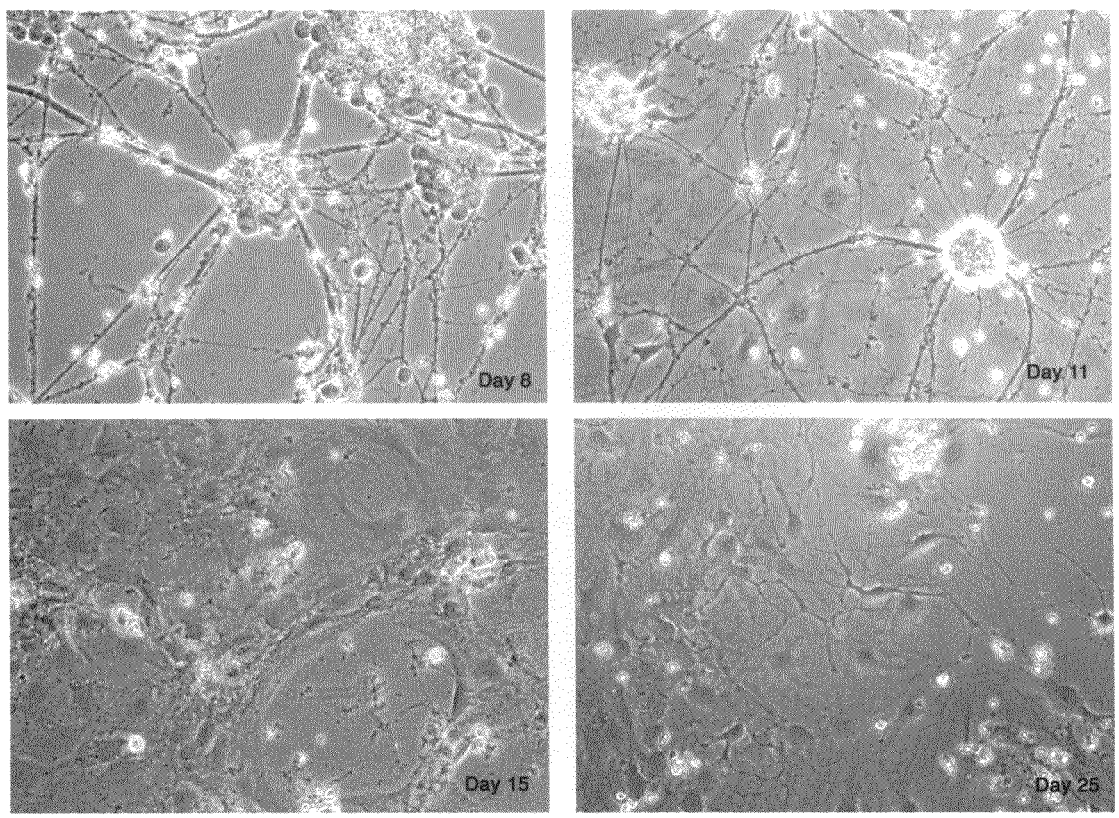

Results:

BoNT Sensitivity of RSC Cells:

In order to determine when the spinal cord cells were differentiated and ready and sensitive to BoNT, the cells were periodically examined by light microscopy at 5-25 days after plating (FIG. 8). After 15 days, the appearance of cells did not change significantly, and no significant change in BoNT/A sensitivity was observed, even after 8 months (data not shown).

Figure 9:
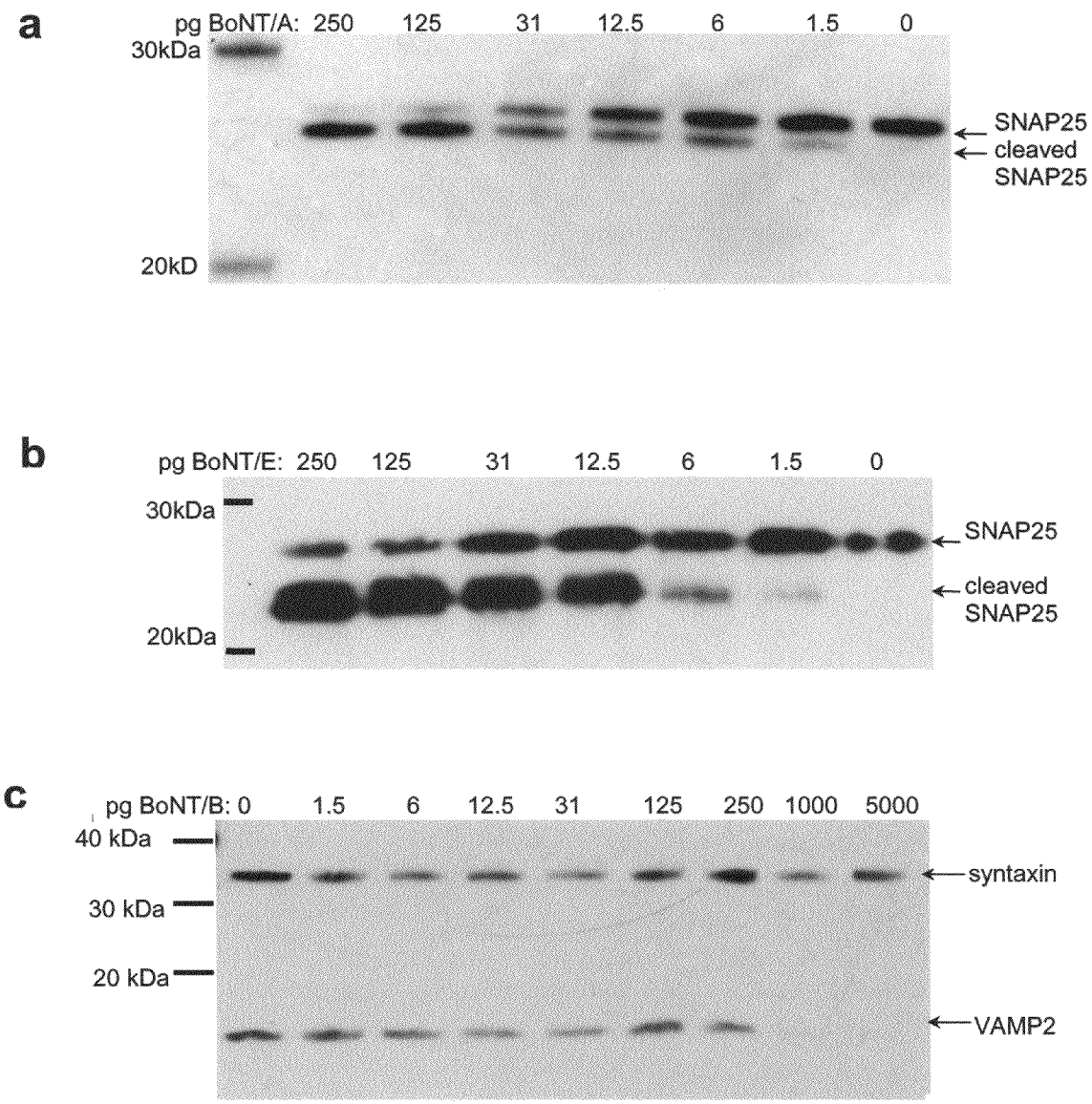

To determine BoNT sensitivity, RSC cells were exposed to serial dilutions of BoNT/A, B, and E, incubated for 48 h, and cleavage of the target protein (SNAP25 for BoNT/A and E, and VAMP/synaptobrevin for BoNT/B) was examined by Western blot. A weak band corresponding to the SNAP25 cleavage product was observed with as little as 1.5 pg of BoNT/A or E (33 fM or approximately 0.1 mouse $LD_{50}$ units), and the relationship of cleaved versus full length SNAP25 with increasing BoNT concentration was linear in the range of 6-126 pg BoNT/A and 12.5-125 pg BoNT/E. At 125 pg BoNT/A (2.8 pM; ca. 10 mouse $LD_{50}$ units), ca. 70-75% of the SNAP25 was present in the cleaved form (FIGS. 9a and b).

BoNT/B intoxication of the cells was determined by using an antibody that recognizes only the full-length VAMP/synaptobrevin, but not the BoNT/B cleavage product (Synaptic Systems) (FIG. 9c), and syntaxin as a loading control. A decrease in the VAMP/synaptobrevin band was apparent at 250 pg BoNT/B (5.5 pM), and the band had almost completely disappeared at 1 ng BoNT/B (22 pM).

Detection of Neutralization of BoNT/A Activity by Human Sera in the RSC Assay:

To determine whether the assay correlated with clinical data of BoNT/A resistance of patients, 15 human serum samples were tested in a blinded manner. In this assay, 75 µl of the serum samples were mixed with 125 pg of BoNT/A in a total volume of 0.3 ml, and the mixture was pre-incubated at 37° C. for 1 h before exposure to the RSC cells.

Figure 10:
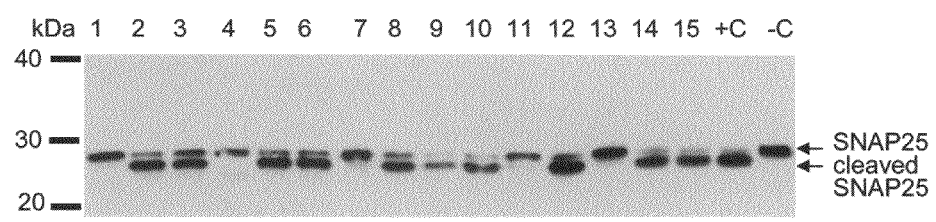
Figure 10:
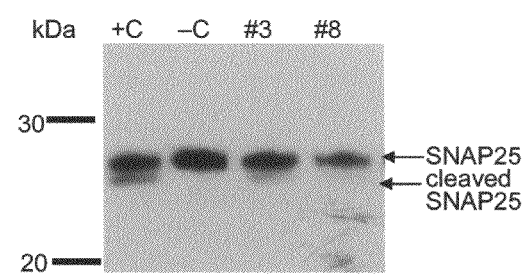
Figure 11:
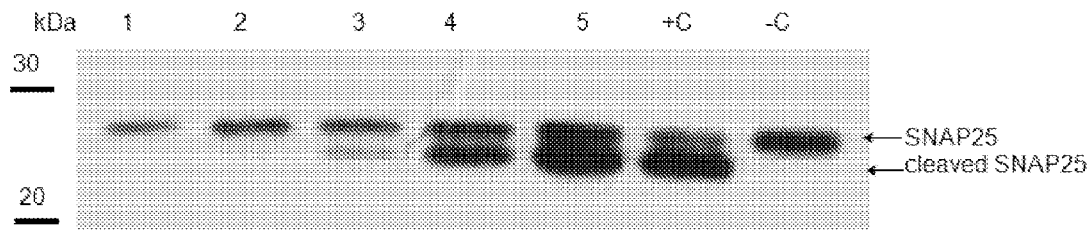
Figure 11:
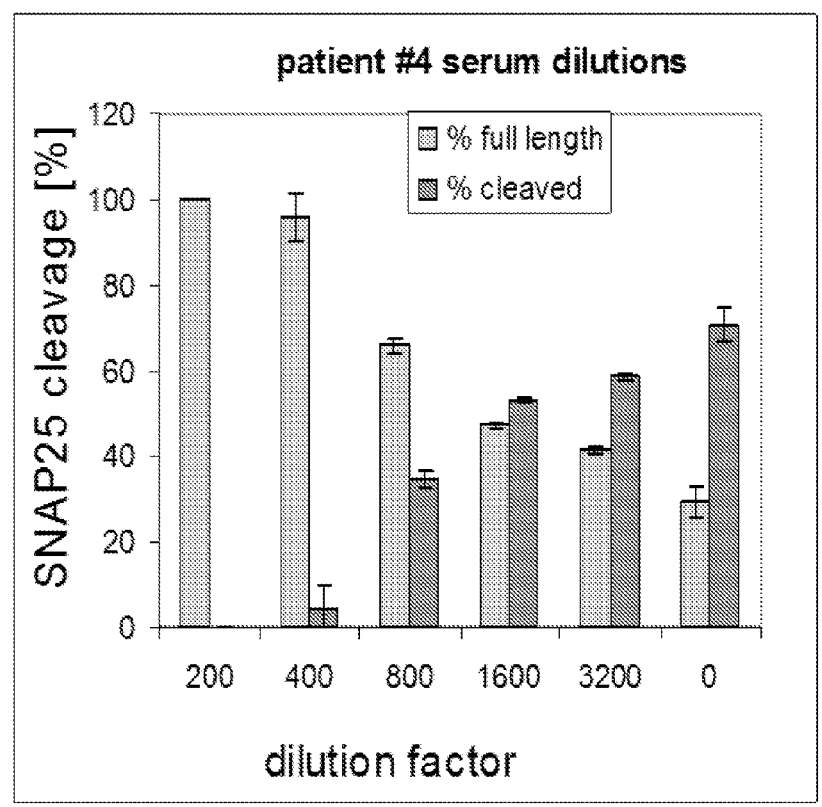

In 5 of the 15 samples (#1, #4, #7, #11, and #13), no SNAP25 cleavage product was detected on the Western blots, indicating complete protection against BoNT/A induced SNAP25 cleavage (FIG. 10). In two samples (#3 and #8), only a small reduction in the ratio of cleaved versus full length SNAP25 was observed, and this was confirmed by repeating the assay in triplicates (not shown). Additionally, in a repeat RSC assay using only 12.5 pg of BoNT/A and 75 µl of serum #3 and #8, nearly all full length SNAP25 was detected on the Western blot, indicating protection against SNAP25 cleavage. No protection was observed using these two serum samples in an independently performed mouse lethality assay. In all other samples, no significant difference to the control (no serum) was observed. These data were in excellent agreement with clinical findings of resistance to BOTOX® treatment and remote point testing (see Table 2).

Determination of Sensitivity of the RSC Assay for Antibody Detection:

In order to determine the detection limit of this assay for neutralizing serum antibodies, serial dilutions of serum #4 were examined in the RSC assay in a blinded manner. Serum #4 was chosen because it appeared to have the highest titer and therefore allowed for analysis of the greatest dilution range. In parallel, the serum was titered by mouse lethality assay using the same amount of BoNT/A (125 pg or ca. 10 $LD_{50}$ units in 0.3 ml). The MLA was able to detect protection against BoNT/A induced death with serum dilutions of up to 1:120 (50% of mice died). Higher dilutions resulted in death of all mice tested (data not shown). One International Unit (IU) can neutralize $10^4$ mouse $LD_{50}$ Units of BoNT/A, therefore 0.3 ml of this serum neutralizes 1200 units, and the titer of the serum was estimated to be 0.4 IU/ml.

Using the RSC assay, significant protection against cleavage of SNAP25 was observed with serum dilutions of up to 1:1600. The relationship of serum amount and SNAP25 cleavage was linear within the range of serum dilutions of 1:200 and 1:3200, with a Pearson coefficient of −0.99 (FIG. 4). This indicates that this assay can be used to reliably and quantitatively determine the neutralizing BoNT/A antibody titers of human sera.

Based on these data, the titers of 3 serum samples were determined using this assay. All three serum samples were derived from patient #11 at different times after a test injection with 20 Units of Botox®, which the patient was non-responsive to. The titer was similar in all three serum samples and was estimated at 0.006-0.0075 IU/ml by correlation to data from dilutions of serum #4. An independently performed mouse lethality assay confirmed the titers of these samples (data not shown).

Discussion:

The cell-based BoNT assay presented here is specific and highly sensitive for BoNT/A, B, and E potency determination (about 0.1 mouse $LD_{50}$ units of BoNT/A' and E), and is the most sensitive assay reported in quantitative detection of neutralizing human serum antibodies to BoNTs. Compared to the mouse bioassay/lethality assay, this assay has the following advantages: 1) no need for large numbers of animals and exposure to pain and distress, 2) higher specificity due to the use of BoNT substrate cleavage as endpoint, 3) higher sensitivity in detection of neutralizing antibodies, 4) excellent reproducibility with low standard deviations, and 5) increased safety for laboratory workers as toxin does not need to be handled in syringes. While this assay still requires the use of relatively few animals in order to prepare the primary spinal cord cells, one rat on average yields enough cells for 72 assays, and a small number of replicas per sample (3-5) are sufficient to yield reliable results. Currently, the time required to complete the assay is approximately equal to the mouse bioassay (3-4 days). Future refinements of this assay will determine optimal parameters such as toxin concentration and preparation, number of replicas per sample, incubation time, buffer composition, serum sampling and storage, etc.

Other assays utilizing primary spinal cord cells have been reported previously; however, they appear to either lack the sensitivity required to be a valid replacement of the mouse bioassay, do not utilize a BoNT specific endpoint, or are impractical for routine testing [Stahl, A. M., et al. (2007) J. Biomol. Screen. 12:370-377; Hall, Y. H., et al. (2004) J. Immunol. Methods. 288:55-60; Keller, J. E., et al. (1999) FEBS Lett. 456:137-142; Keller, J. E., et al. (2004) Biochem. 43:526-532; Neale, E. A., et al. (1999) J. Cell. Biol. 147:1249-1260; and Lalli, G., et al. (1999) J. Cell. Sci. 112:2715-2724]. It has been reported that most sera of patient's who are refractory to BoNT treatments have titers in excess of 0.001 IU/ml [Goschel, H., et al. (1997) Exp. Neurol. 147:96-102]; however, lower concentrations still may have an impact on clinical response. Only one assay previously reported is sensitive enough to detect 0.001 IU/ml [Hall, et al., 2004, J. Immunol. Methods 288: 55-60.]. However it utilizes a non-BoNT specific endpoint (neurotransmitter release), and requires the use of radioisotopes. The assay described here utilizes a highly specific endpoint (BoNT specific substrate cleavage), can reliably quantify serum titers down to 0.0003 IU/ml, and can detect even lower levels by decreasing the quantity of toxin employed. In fact, the sera of two patients examined contained titers too low to be detected by the mouse lethality assay or by the RSC assay using 125 pg of BoNT/A, however, the use of only 12.5 pg of BoNT/A resulted in the detection of neutralizing antibodies (FIG. 10). These patients were resistant to BOTOX® treatments, although they had not received any treatments in over ten years. This emphasizes the clinical importance of detecting very low antibody titers (below 0.001 IU/ml). The ability to detect such low levels of antibodies may also prove extremely useful in monitoring of patients for developing BOTOX® resistance.

Future studies are underway analyzing a larger number of serum samples to further validate and refine this assay. Even though this assay currently has lower sensitivity for BoNT/B (about 20 mouse $LD_{50}$ units) and has not yet been tested in BoNT/B antibody detection, the assay is likely adaptable to BoNT/B antibody detection.

Example VI

Using ICWs for Cell Based Assays: Evaluation of In-Cell Westerns for Botulinum Neurotoxin Detection In Vitro Introduction A cell based assay for botulinum neurotoxin (BoNT) activity with very high sensitivity has been developed using primary rat spinal cord cells (Examples I-V). In response to BoNT serotypes A or E, the membrane-bound (but cytosolic) molecule SNAP25 (synaptosome-associated protein of 25 kDa) is cleaved, resulting in the inability to exocytose synaptic vesicles at the neuromuscular junction. This activity causes the paralysis associated with botulism, but also can be used clinically to treat neurological diseases and conditions, such as dystonia or muscle spasticity, in which muscles are continuously contracted. However, the effectiveness of using BoNTs as a treatment is often reduced or eliminated because of the formation of antibodies in patients who have received prior treatments. This assay was developed as a sensitive, cell based assay which requires all the steps of intoxication, that could be used to monitor patients' sera for the presence of neutralizing antibodies, without the need for mouse lethality bioassays to be performed (where toxin and antibody mixtures are injected into several mice, which are monitored for signs of paralysis until death).

The cell-based assay developed can be used to detect neutralizing antibodies in human serum samples using primary rat spinal cord cells seeded in 96 well plates and exposed to toxin/serum mixtures. The current readout via Western blot requires lysate preparation from each individual well, manually loading and running gels, blotting, staining and analysis via densitometry for quantitative analysis of the level of cleaved SNAP25. While the assay is very sensitive and can detect amounts of toxin in the 1-100 fM range, it is fairly labor intensive, requiring several days for the readout to be obtained.

In this Example we have evaluated the feasibility of using In Cell Western (ICW) assays to detect cleaved SNAP25 in situ, with less sample handling, shorter time until the readout is obtained, and also more easily scaled up to high throughput analyses. Ideally the sensitivity of this assay would be as high as that using Western blots or potentially higher and would be less resource intensive (no gels, no membranes, less reagent usage, etc).

Evaluation of the method for using ICWs in vitro to detect cleavage of SNAP-25 in response to a dose response of BoNT A was performed using primary rat spinal cord cells as well as a mouse neuroblastoma cell line previously shown to be sensitive to BoNTs (though less so than the primary cells), neuro2a. The results of titrations of antibodies and toxin dilutions, optimization of fixation protocols and comparisons of ICW results with Western blots are presented below.

Materials

Licor blocking buffer was used unless specified for all blocking and antibody incubation steps (Licor Biosciences, #927-40000). The primary antibody used for all experiments was a monoclonal antibody to cleaved SNAP25 (R&D, mouse monoclonal (MC-6053)), while the secondary was a goat anti mouse 800 IR dye conjugated antibody (Rockland Inc., #610-131-121, IRDye 800CW conjugated goat anti mouse). Nuclear staining was done using ToPro3 (Molecular Probes). Plates were scanned on a Licor Odyssey infrared laser scanner and analyzed for integrated intensity from the nuclear stain (as a control for cell number), and from the SNAP25 antibody.

Results and Methods

Primary Rat Spinal Cord Cells

Spinal cord cells were prepared as previously described and plated in 96 well plates at a density of 75,000 cells per well. The cells were allowed to differentiate for at least 2 weeks before being used in the assay. Neuro-2a cells were plated into 96-well plates the day prior to toxin exposure, to about 40-50% confluency. The cells were treated with specified amounts of toxin in culture medium (neurobasal supplemented with B27, glutamax, and penicillin/streptomycin, Invitrogen) for 48 h. After toxin exposure, the cells were washed briefly with ice-cold PBS, and fixed on ice with 4% PFA in PBS for 20 minutes. After four 5 min. washes with 50 µl/well of 0.1% Triton X-100 in PBS, 40 µl of blocking buffer (Licor blocking buffer with 0.1% Tween-20) was added for 4 h at 4° C. The cells were then exposed to 40 µl/well of the primary antibody at a dilution of 1:50 in blocking buffer overnight at 4° C. Wells were washed 3 times with PBS, 0.1% Tween-20 for at least 7 minutes each wash, then the secondary antibody was added at a 1:250 dilution in blocking buffer for 45 minutes at room temperature in the dark. After 2 washes with PBS, 0.1% Tween-20, nuclei were stained using ToPro3 (Molecular Probes) at a 1:500 dilution in PBS for 10 minutes at room temperature in the dark. The cells were then washed twice with PBS and tapped dry before scanning.

Figure 12:
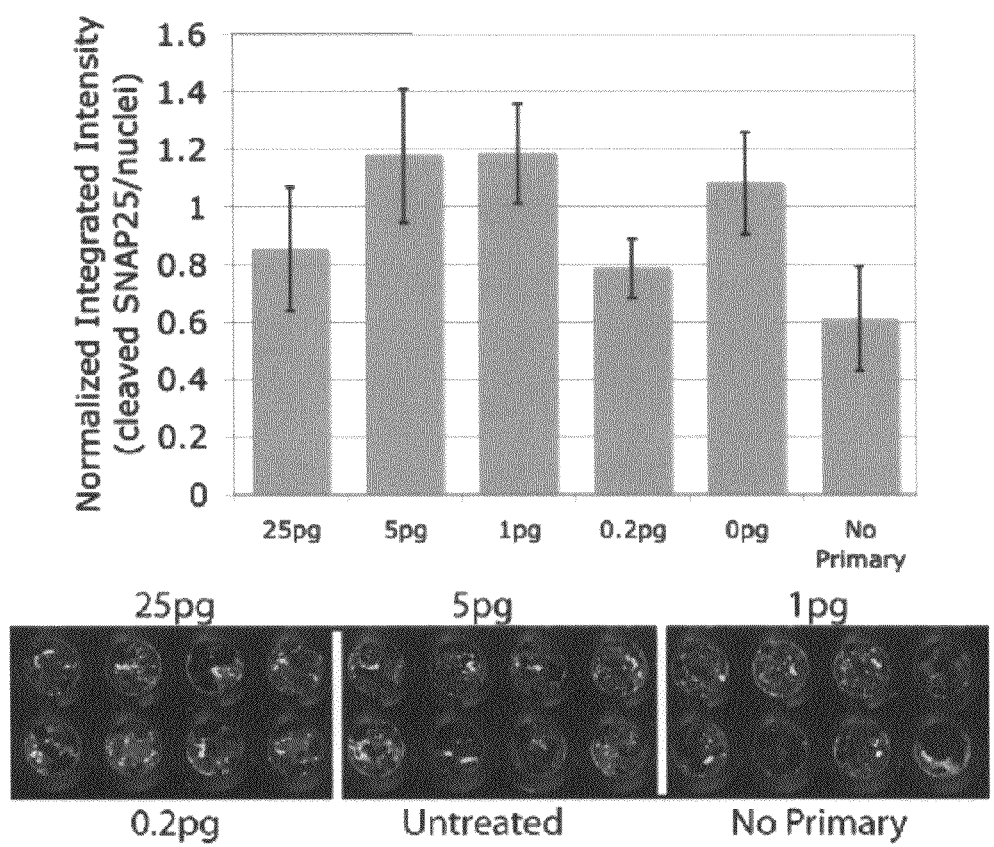

FIG. 12 shows the initial results of ICWs using spinal cord cells for the BoNT assay. Unfortunately, there was so much non-specific fluorescence that the dose response was obscured and no significant signal above the background level was seen (background is no primary condition). These cells do not grow in a monolayer, but instead grow in three dimensional clumps. The scanner has a 300 µm focal distance, so the three-dimensionality of these cells shouldn't be an issue from an optical perspective. However, it seems that for some reason there is either a lot of autofluorescence even in the IR range of the scanner, or something about how these cells grow makes it hard to wash out the excess secondary antibody.

Figure 13:
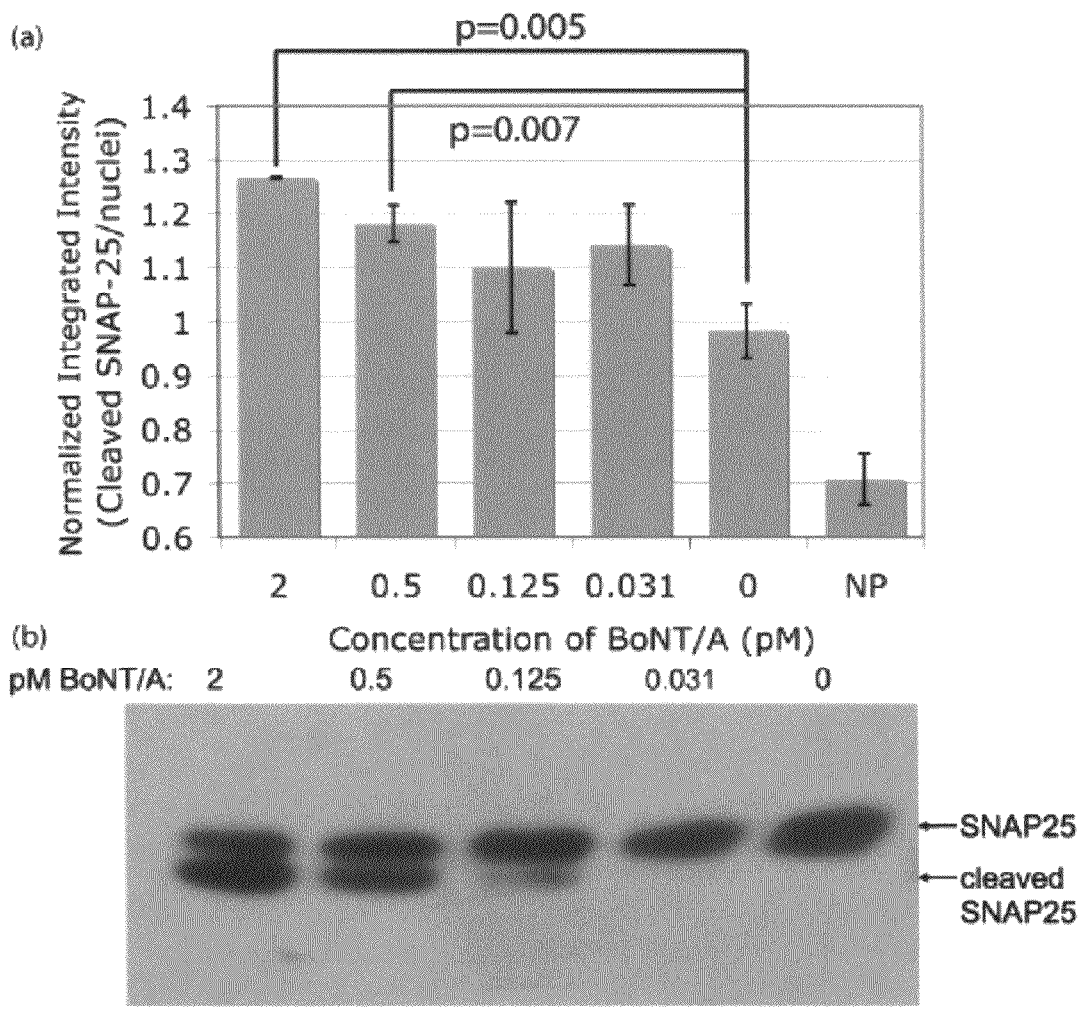
Figure 14:
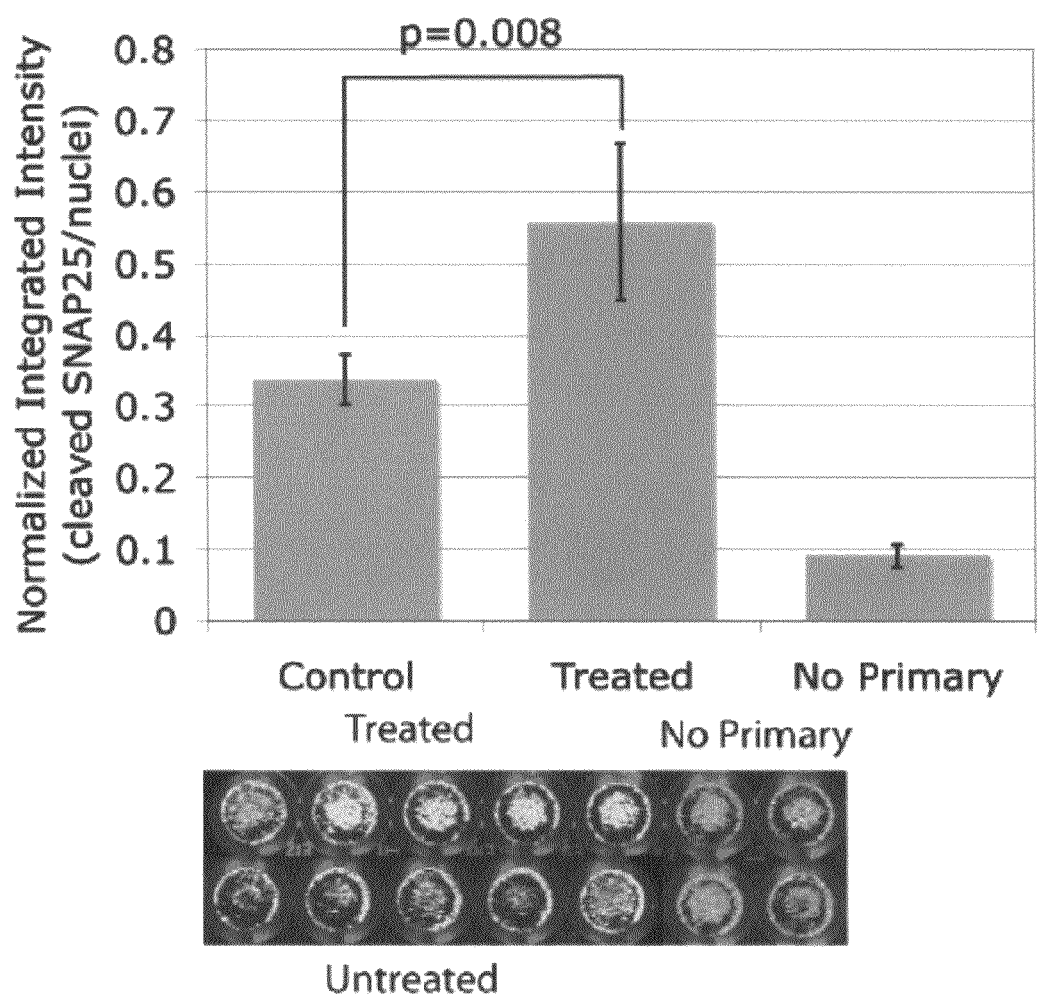

After the fixation and staining protocol was improved using neuro2a cells (described later), the adjusted protocol was performed again on primary cells. This protocol used a 10 minute fix with 4% PFA on ice, one 7 minute wash with 0.1% Triton X-100 in PBS, blocked for 1 hour at room temperature, then incubated with the primary antibody at 1:25 for 1 hour in blocking buffer at room temperature, and the secondary at 1:100 in blocking buffer for 45 minutes in the dark at room temperature. All other steps were the same as described above. These results are improved, and shown in FIG. 13. The Western blots done alongside the ICWs are also presented as a comparison to the current technique used for this assay.

Neuro-2a Cells

Neuro-2a cells were maintained at 37° C., 5% CO2 in a humidified atmosphere in DMEM medium (DMEM glutamax supplemented with 0.1 mM MEM non-essential amino acid solution, 10% fetal bovine serum, 50 U/ml penicillin G sodium, 50 µg/ml streptomycin sulfate, and 0.15% sodium bicarbonate (all from Invitrogen)). For the toxin assays, cells were seeded into 96-well plates in DMEM medium, and after 24 h toxin was added either in DMEM medium or in culture medium as indicated. For un-treated cells, an equal volume of the same medium was added.

To verify that the primary antibody can be used for this type of assay, neuro-2a cells either treated with 20 nM BoNT/A for 72 h in culture medium, or untreated were evaluated using the ICW technique. The same protocol was followed as described for the spinal cord cells (the initial protocol).

This data shows that ICWs will work for determining levels of cleaved vs uncleaved SNAP-25 in neuro-2a cells. However, because the control cells had a relatively large normalized integrated intensity over background, the elimination of nonspecific staining of the primary would be important to increase the sensitivity of the assay.

Figure 15:
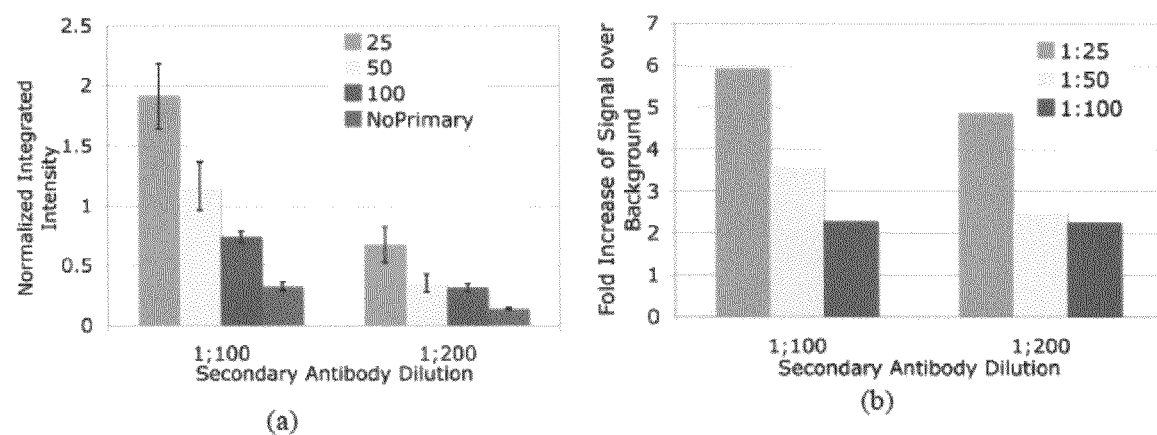

A titration of the primary and secondary antibody was performed on cells treated with 20 nM BoNT/A in culture medium and compared to un-treated cells. However, only valid data sets were obtained from treated cells. Also, these cells were stained using the same protocol for the previous experiment with the primary and secondary antibody dilutions specified in FIG. 15.

The 1:100 secondary antibody and 1:25 primary antibody dilution gave the highest potential signal with respect to background, which should provide the potential for the most sensitive readout because it would allow a wider range of cleavage to be detected before signals begin to be not significantly different from background. With primary antibody dilutions lower than 1:100, the 1:100 secondary dilution gave significantly higher signal from treated cells with respect to background than 1:200.

The experiment was repeated with a dose response of toxin to determine if the method could distinguish different doses, and how the results compared to traditional Westerns. In this case, cells were exposed to 100, 50, 25, 12.5, and 0 nM BoNT/A in culture medium for 48 h. The cells were fixed and stained with the standard protocol with a 1:75 dilution of the primary and 1:100 dilution of the secondary. The signal from all treated cells was significantly higher than both untreated cells and the no primary/background conditions.

Despite very low cell density, the results of the ICW proved that the technique could be very sensitive, with even the 12.5 nM dose being significantly higher than untreated. However, ICW results are more sensitive when cell densities are higher, so it would be expected that even lower doses of toxin could be detected with cells of higher density.

Lysates were prepped from wells of the same set of cells with the same toxin treatments and the Western blots were stained two ways. PVDF membranes were blocked and stained with a total SNAP-25 antibody and analyzed using chemiluminescence. Additionally, a second membrane was blocked in Licor blocking buffer, then stained with the cleaved SNAP-25 antibody used for the ICWs at 1:100 dilution in Licor blocking buffer with 0.1% Tween-20 overnight at 4° C. The membrane was then washed with PBS with 0.1% Tween-20, and incubated at room temperature with a goat anti mouse 800 IR dye secondary antibody at 1:15,000 for 45 minutes with shaking. After washing the membrane was allowed to dry and scanned on a laser scanner.

This antibody does not work well on a Western blot, but gives relatively consistent results with both the ICW and the Western from a total-SNAP25 antibody if only one band is considered. Also, Western blots with the cleaved SNAP25 antibody proved to not have a downward sloping dose response (e.g., the 12.5 nM cells were higher than the 50 nM dose), consistent with the ICW results. However, a better dose response with ICWs and Western blots done side by side would be important to better determine how sensitive this assay is. Also, by optimizing both the cell seeding and fixation protocols, more reliable, sensitive results could likely be obtained.

To begin to optimize the signal, a lighter fixation protocol was tested on cells treated with 30 nM BoNT/A in DMEM medium for only 24 hours to prevent significant cell death due to over-growth of cells prior to fixing. DMEM medium was used instead of the serum-free culture medium to provide optimal conditions for cell health. In this case a 10 minute fix with 4% PFA was performed, and only two, 7-8 minute triton washes before blocking. The resulting signal was significantly better than previous results and showed a much larger difference between treated and untreated cells.

If the level of background was reduced, then a wider range of doses could be distinguished and potentially lower levels of cleavage detected. To reduce background due to non-specific staining of the secondary antibodies, several different blocking conditions were tested on un-treated neuro-2a cells, and the normalized integrated intensity of the wells without the addition of primary antibody determined.

SNAP-25 is a cell membrane protein (though intracellular), and likely does not require several washes with permeabilizing buffer in order to make it available for binding. Also, because it is at least partially soluble in the membrane, it could be removed completely by several washes with the buffer. To minimize this, another test of fixation protocols was done with a 10 minute PFA fix on ice, with either 1 or 2, 7 minute washes with 0.1% Triton X-100. Concentrations of toxin of 20 nM or 10 nM in DMEM medium were tested and compared to untreated cells for each condition. Additionally, dilutions of the primary antibody with the new fixation protocols was done, using either 1:25 or 1:50 dilutions.

From this data, the best sensitivity seems to be with a 10 minute, 4% PFA fix on ice, with 1 triton wash, and a 1:25 dilution of the primary, and a 1:100 dilution of the secondary, all after a 24 hour exposure to toxin. The sensitivity in this ICW was very high, considering that on a Western blot performed in parallel only very little cleavage could be detected with 20 nM BoNT/A.

Optimization of Toxin Exposure of Neuro-2a Cells

Figure 20:
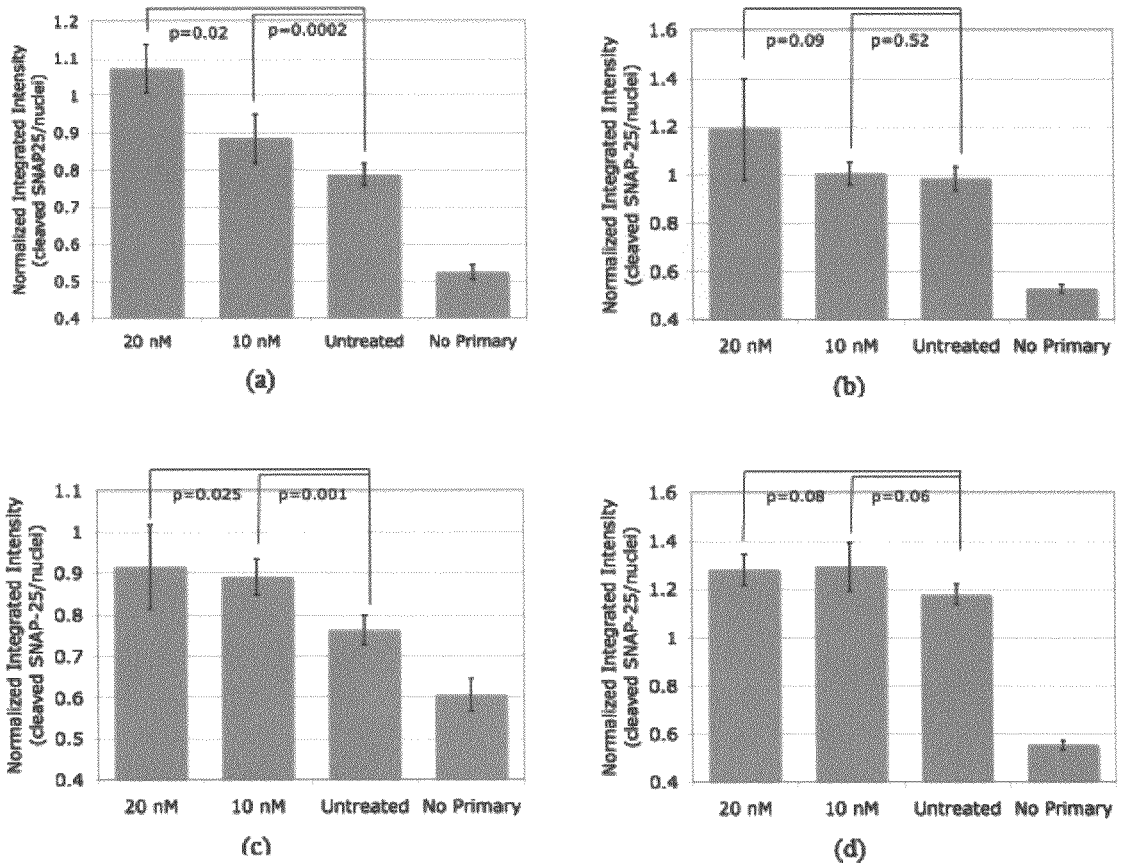

In order to determine the best conditions for a 24 h toxin exposure of neuro-2a cells, the cells were exposed to 80, 40, 20, 10, and 0 nM BoNT/A in either DMEM medium or in culture medium for 24 h. The cells were harvested in NuPAGE LDS sample buffer (Invitrogen) and SNAP25 cleavage was analyzed by Western blot as described before. All samples were done in triplicates, and one representative Western blot is shown (FIG. 20). These data clearly demonstrate that toxin exposure in culture medium results in significantly greater cleavage of SNAP25 than in DMEM medium.

Validation Via ICW and Paired Western Blots

Figure 21:
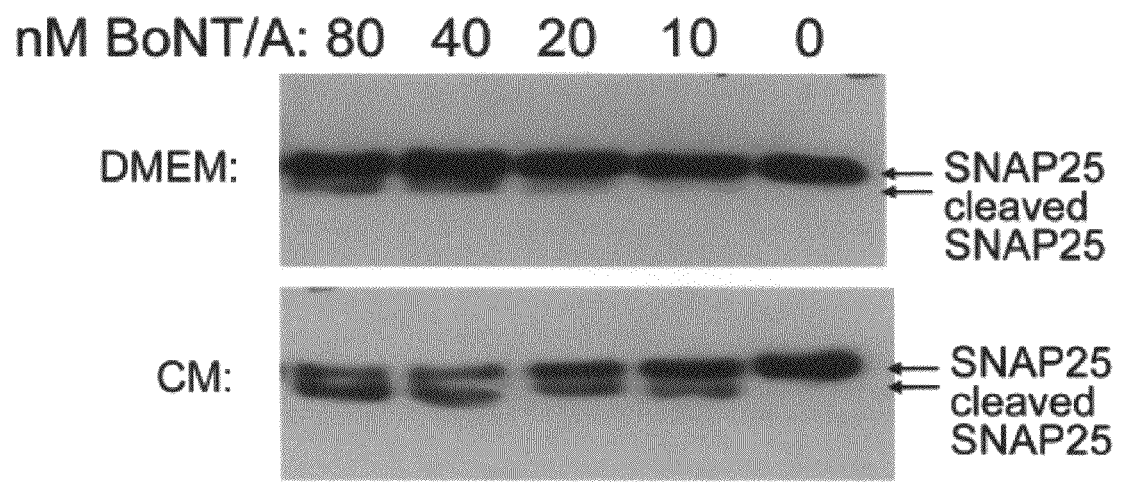
FIG. 21 depicts the dose response of neuro2a cells with two different exposure media. Significantly more cleavage can be detected when cells are exposed to the toxin in culture medium than when the same experiment is performed with DMEM.

In Cell Westerns are essentially quantitative immunocytochemistry and thus antibodies are better validated via both immunocytochemistry and Westerns to ensure specificity and that the antibody recognizes the antigen in the correct conformation. Antibodies tested only on Western blots with denatured and reduced proteins won't necessarily give the same results as an ICW (or can potentially give no results depending on the antigen). However, the conformation of the protein isn't necessarily native in ICWs because of the fixation and permeabilization protocol used. It is important to both verify via immuncytochemistry with positive and negative controls, along with no primary background controls that the antibody does bind the protein, with the expected localization, and that the secondary to be used does not cause significant background (FIG. 21). By keeping exposure times, objectives, magnifications and image processing steps the same for each condition, we can visualize what is quantitated by the laser scanner.

Figure 16:
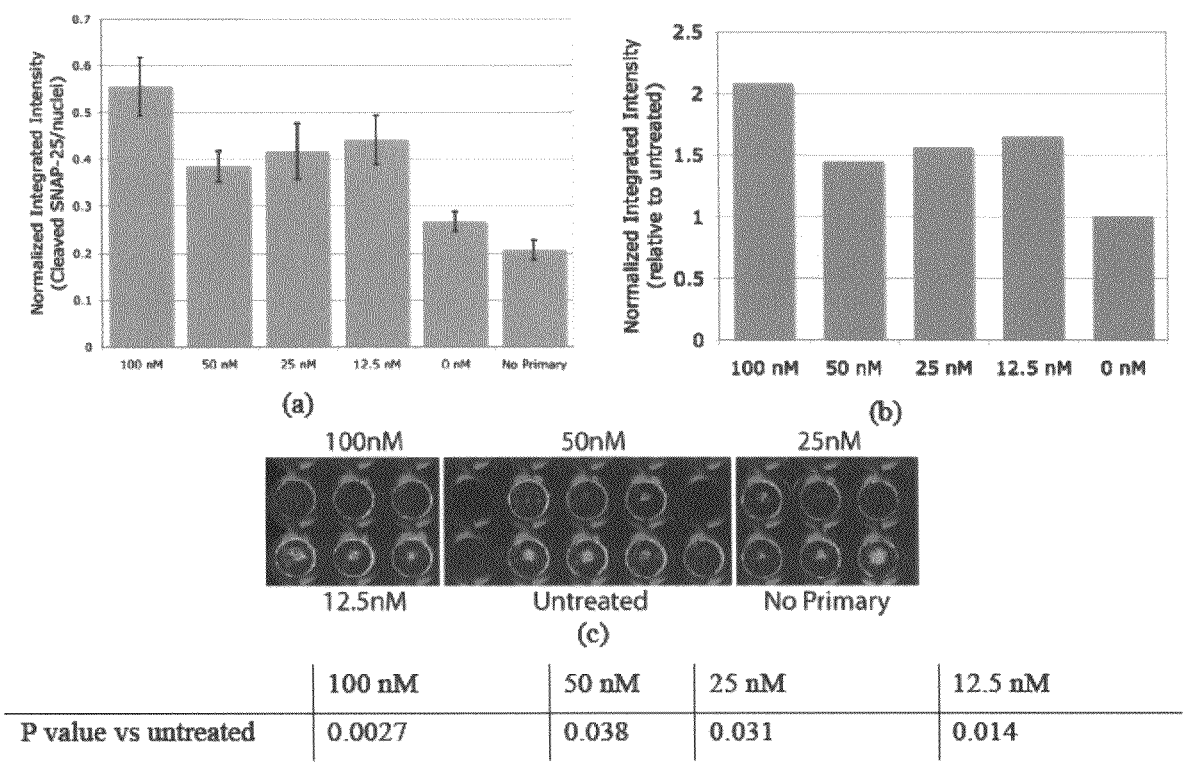
Figure 17:
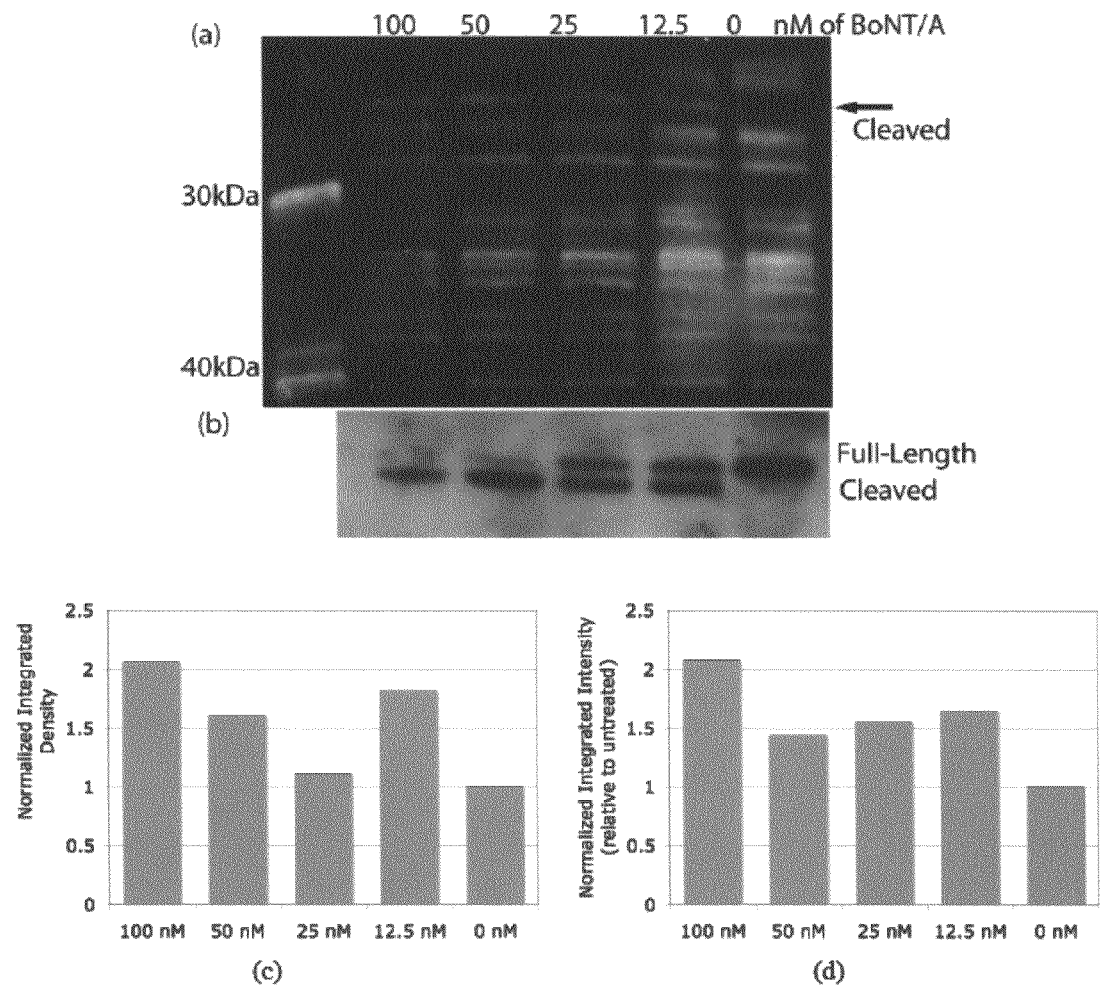
Figure 18:
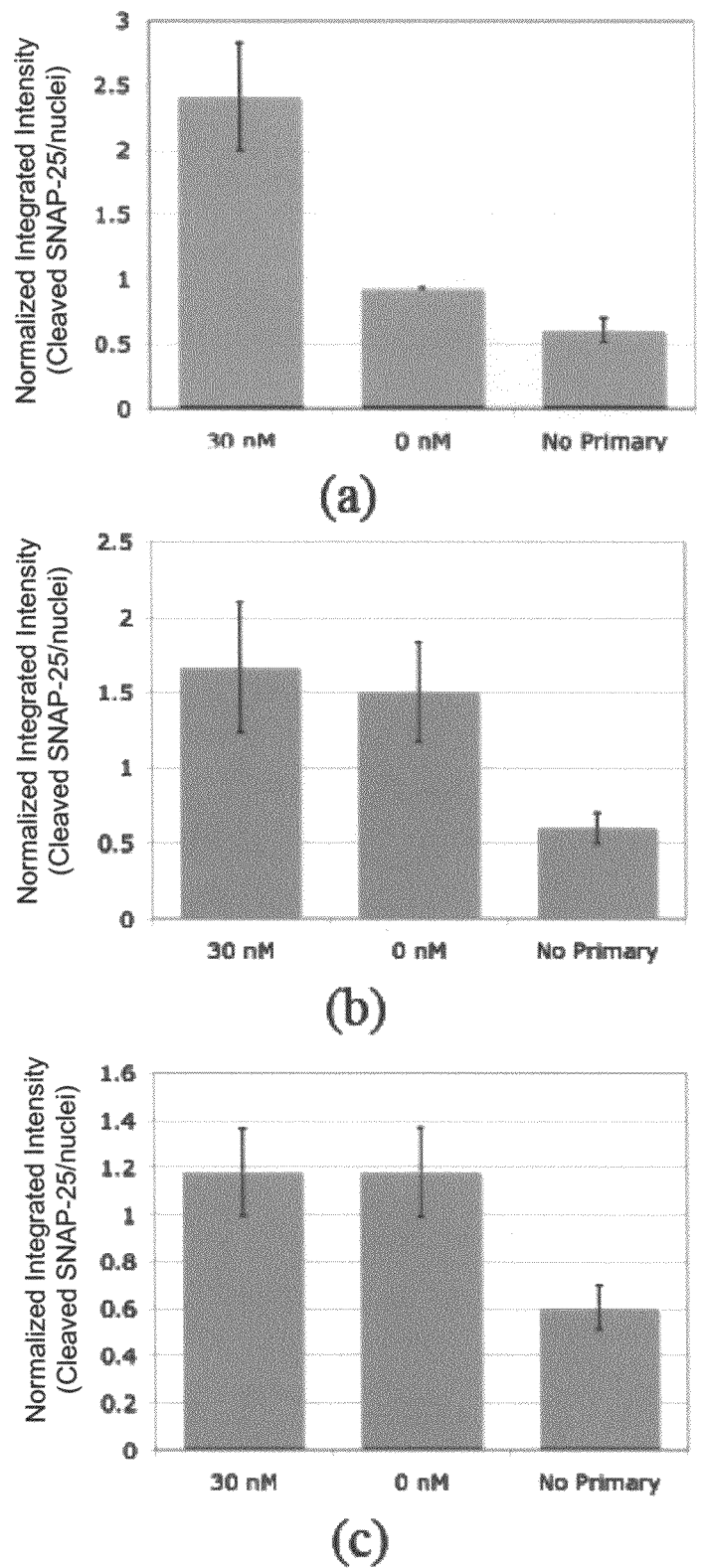
Figure 19:
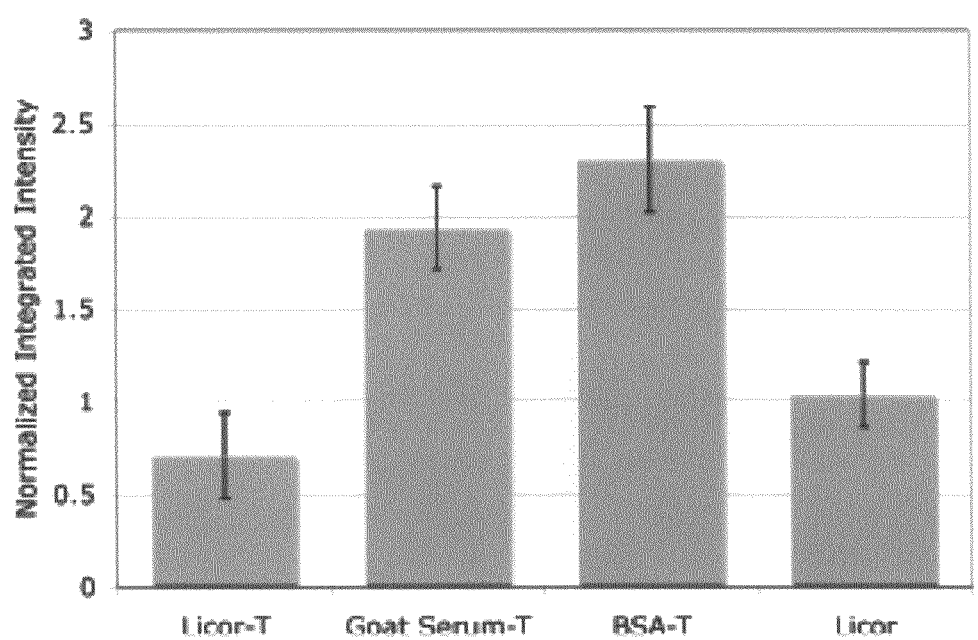
Figure 22:
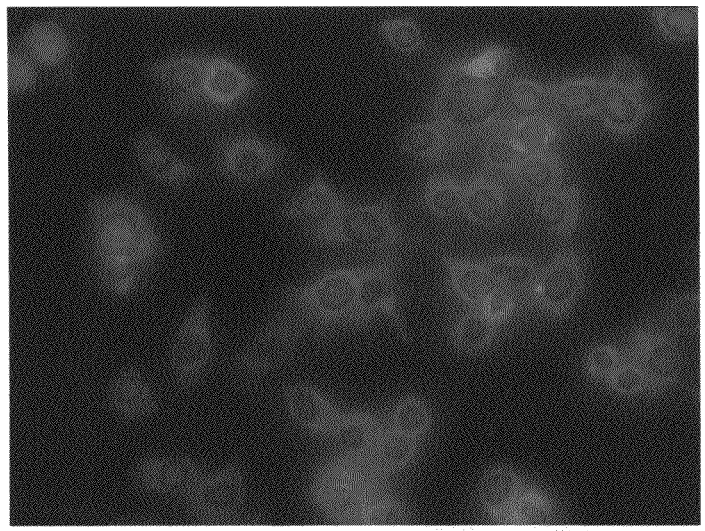
FIG. 22 depicts neuro2a cells with 81 nM toxin—ICC data (a) 81 nM toxin exposure for 24 hours, (b) untreated cells, and (c) no primary control cells, all images at the same magnification and exposure length.
Figure 22:
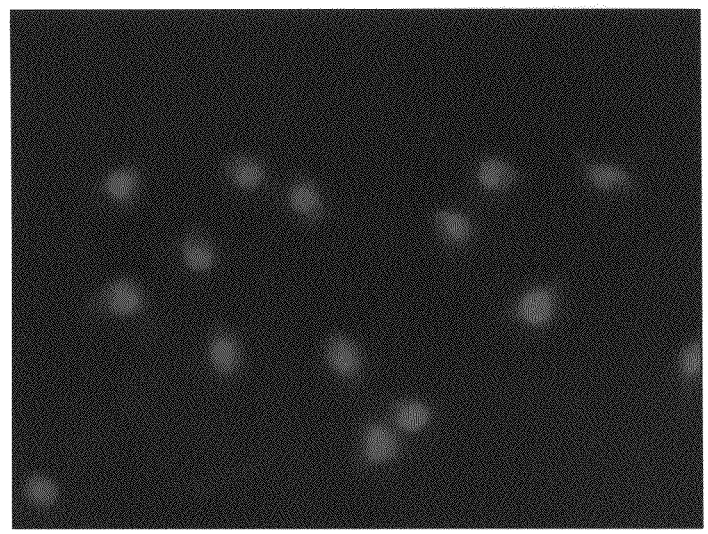
Figure 22:
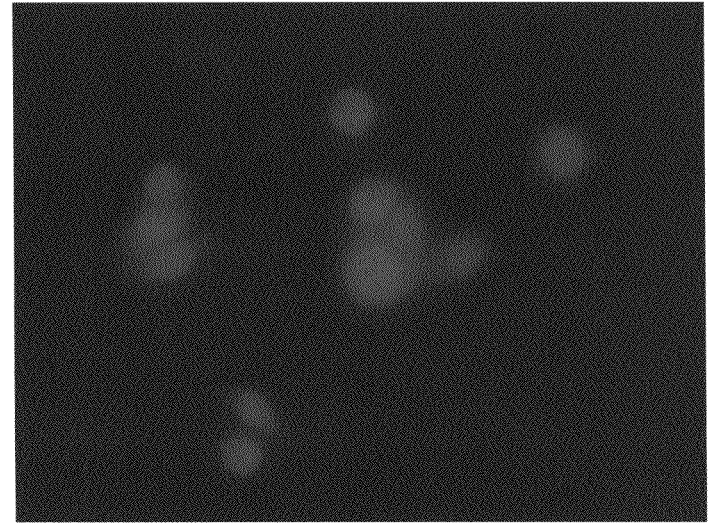

Paired Western blots were performed with a dose response of toxin to compare sensitivity of each type of assay. Because the antibody used for ICWs is not well suited for Western blots (see FIG. 16), the ICW results were compared to the current technique being used which uses an antibody to total SNAP-25 and relies upon band separation for determining levels of the cleaved form. Neuro-2a cells were exposed to 81, 27, 9, 3, 1, and 0 nM BoNT/A in culture medium for 24 h, in replicates of at least 6. Three wells of each concentration were lysed for Western blots analysis, and 3 or 4 wells were fixed and stained for ICWs (with the 10 minute fix, 1 triton wash, 1:25 primary, 1:100 secondary) the results are shown in FIG. 22.

While the lowest concentration that provided significantly higher signal than untreated cells was 27 nM (previously we detected down to 9-10 nM), it appears that the Western blots were unable to detect much cleavage in the 9 nM sample as well. This indicates that although the cell density, toxin exposure time, etc are variable at this point, the ICW technique itself has been consistently as sensitive or more sensitive as traditional Western blots for the neuro2a cells.

Discussion

Although the ICW results from spinal cord cells proved to be not as sensitive as traditional Westerns, it was shown that it will be a viable method after optimization of the protocol for those specific cells.

The neuro2a cells do grow in a monolayer, and the ICWs proved to be at least as sensitive as traditional Western blots, if not more so. If the issues surrounding cell density and toxin treatment length were eliminated, then this technique would likely provide a reliable and simple method for analyzing levels of cleaved SNAP-25 after BoNT exposure in situ. This method could likely be more sensitive than traditional Western blots, without the limitations and caveats of densitometry, and also more amenable to higher throughput assays.

Ideally a cell line that was more sensitive to BoNTs than neuro2a cells could be used that would grow easily and quickly in a monolayer so that lower levels of toxin could be detected. In this case, ICWs could provide even better detection than traditional Westerns and would be a technique that could be implemented with widely available resources (e.g., cell lines, antibodies, 96 well plates and plate readers).

This assay may lend itself well to adaptation to the high throughput microfluidic platform. Reductions in cell number per replicate would allow a larger number of samples to be screened with nearly 8 fold less toxin and patient sera samples than even 96 well plates require. Also, because the cellular response being used in this assay is not dependent on cell proliferation, or other aspects of cell function that have been shown to be altered in microfluidic devices, it may be an example of an assay that would provide similar results regardless of scale. ICW readouts for toxin exposure, provide a significant improvement in the time required for the readout to be obtained, and also are a less labor- and reagent-intensive method for analyzing the results of the assay than running many traditional Westerns.

Optimization of ICW Assay for Spinal Cord Cells

To optimize the ICW technique for the spinal cord cells, one can use the information gained using neuro2a cells as a basis. The ICW technique requires several important steps: 1) fixation of the cells, 2) permeabilization, 3) blocking, and 4) staining. To optimize this protocol for spinal cord cells, ideally each of these four major steps would be independently optimized allowing for the highest sensitivity measurement to be made using these cells. Fixation of the cells can be optimized by using different fixation conditions, such as changing the percentage of paraformaldehyde used (to a range of 1% to 4%), comparing ethanol/methanol fixation methods to paraformaldehyde, changing the amount of time exposed (to 5 min-30 min), incubating on ice during fixation or at room temperature. It is likely that lower percentages and less time on ice will work the best. Fewer washes to permeabilize with a gentler detergent (such as Tween-20) would likely also help. More washing during staining will also improve the results. By fixing using several different conditions and keeping all other steps the same, the technique that results in the highest sensitivity (the ability to detect the lowest concentration of toxin as compared to the appropriate control, such as untreated cells), should be used.

Similar methods can be used for all of the other steps:
Fixation: One would optimize paraformaldehyde concentration, ethanol/methanol vs paraformaldehyde, incubation times and temperatures;
Permeabilization: One would optimize number of washes, detergent used (Triton X-100 vs Tween-20 for example);
Blocking: One would change the blocking buffers (such as using goat serum vs LICOR blocking buffer), changing blocking times or temperature; and
Staining: One would investigate titrating both the primary and secondary antibody concentrations/dilutions, changing incubation time and temperature, testing different washing times/repetitions.
Once these four steps have been optimized for the spinal cord cells, the sensitivity of ICWs for detection will be suitable for the present invention.

We claim:

1. A method of analyzing a sample for the presence or activity of botulinum neurotoxin (BoNT) or antibodies specific for botulinum neurotoxin, comprising the following steps:
    a) preparing primary non-human mammalian or avian spinal cord cells in media that contain no serum or growth inhibitors, and
    b) exposing the cells to a test sample, in parallel with a control sample, and examining the extent of cleavage of the intracellular neuronal target protein in both the test and control sample.

2. The method of claim 1 wherein the cells are rat cells.

3. The method of claim 1 wherein the sample is a biological sample.

4. The method of claim 1 wherein the biological sample is selected from the group consisting of blood serum, blood plasma, and whole blood.

5. The method of claim 3 wherein the biological sample is blood serum.

6. The method of claim 1 wherein the test sample is evaluated for the presence of neutralizing antibodies.

7. The method of claim 1 wherein the test sample is evaluated for the presence or potency of botulinum neurotoxin.

8. The method of claim 7 wherein the sample comprises non-GMP or pharmaceutical sources of BoNT.

9. The method of claim 1 wherein the assay detects as little as 33 fm of botulinum toxin.

10. The assay of claim 1 wherein the assay detects as little as 0.000091 IU of neutralizing antibody.

11. The method of claim 1 wherein the detection of cleavage is via ICW (In Cell Western).

12. The method of claim 1 wherein the test sample represents a first batch of toxin and is compared to a second test sample representing a second batch of toxin.

13. The method of claim 12 wherein the first and second batches are different formulations of toxins.

14. The method of claim 1 wherein the test sample represents a first botulinum sample and is compared to a second sample which contains a known amount of botulinum toxin.

15. The method of claim 1 wherein the assay is used to determine the pharmacokinetic rate of toxin penetration into cells and target protein cleavage inside the cells.

16. The method of claim 1, wherein the sample additionally comprises an excipient and the method analyzes the effect of the excipient on cleavage of the target protein.

* * * * *